(12) United States Patent
Ippolito et al.

(10) Patent No.: US 11,866,785 B2
(45) Date of Patent: Jan. 9, 2024

(54) TUMOR SPECIFIC ANTIBODIES AND T-CELL RECEPTORS AND METHODS OF IDENTIFYING THE SAME

(71) Applicant: BOARD OF REGENTS, THE UNIVERSITY OF TEXAS SYSTEM, Austin, TX (US)

(72) Inventors: Gregory C. Ippolito, Austin, TX (US); Jonathan R. Mcdaniel, Austin, TX (US); William N. Voss, Austin, TX (US); George Georgiou, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 602 days.

(21) Appl. No.: 16/759,371

(22) PCT Filed: Oct. 29, 2018

(86) PCT No.: PCT/US2018/057961
§ 371 (c)(1),
(2) Date: Apr. 27, 2020

(87) PCT Pub. No.: WO2019/084538
PCT Pub. Date: May 2, 2019

(65) Prior Publication Data
US 2020/0270704 A1    Aug. 27, 2020

Related U.S. Application Data

(60) Provisional application No. 62/578,230, filed on Oct. 27, 2017.

(51) Int. Cl.
*C12Q 1/6886* (2018.01)
*C07K 16/30* (2006.01)
*C12Q 1/6881* (2018.01)

(52) U.S. Cl.
CPC ........ *C12Q 1/6886* (2013.01); *C07K 16/3069* (2013.01); *C12Q 1/6881* (2013.01); *C07K 2317/24* (2013.01); *C07K 2317/565* (2013.01); *C07K 2319/03* (2013.01); *C07K 2319/33* (2013.01)

(58) Field of Classification Search
CPC ................ C12Q 1/6886; C12Q 1/6881; C07K 16/3069; C07K 2317/24
See application file for complete search history.

(56) References Cited

U.S. PATENT DOCUMENTS

| | | | |
|---|---|---|---|
| 6,252,052 B1 | 6/2001 | Stockert et al. | |
| 8,435,775 B2 | 5/2013 | Holliger et al. | |
| 8,519,106 B2 | 8/2013 | Esslinger et al. | |
| 9,090,674 B2 | 7/2015 | Reddy et al. | |
| 9,146,241 B2 | 9/2015 | Lavinder et al. | |
| 9,169,471 B2 | 10/2015 | Holliger et al. | |
| 9,304,065 B2 | 4/2016 | Fowler | |
| 9,708,654 B2 | 7/2017 | Hunicke-Smith et al. | |
| 9,938,511 B2 | 4/2018 | Holliger et al. | |
| 10,175,249 B2 | 1/2019 | Lavinder et al. | |
| 10,323,243 B2 | 6/2019 | Ellington et al. | |
| 10,858,652 B2 | 12/2020 | Ellington et al. | |
| 2002/0076768 A1 | 6/2002 | Kuroita et al. | |
| 2003/0134292 A1 | 7/2003 | Farchaus | |
| 2003/0228616 A1 | 12/2003 | Arezi et al. | |
| 2004/0005594 A1 | 1/2004 | Holliger et al. | |
| 2004/0005599 A1 | 1/2004 | Schoenbrunner et al. | |
| 2004/0009486 A1 | 1/2004 | Sorge et al. | |
| 2005/0069887 A1 | 3/2005 | Kitabayashi et al. | |
| 2005/0272039 A1 | 12/2005 | Yasuda | |
| 2006/0233812 A1 | 10/2006 | Burnie et al. | |
| 2007/0020653 A1 | 1/2007 | Holliger et al. | |
| 2007/0134682 A1 | 6/2007 | Holliger et al. | |
| 2007/0172887 A1 | 7/2007 | Takacs et al. | |
| 2007/0281313 A1 | 12/2007 | Taniguchi et al. | |
| 2009/0098555 A1 | 4/2009 | Roth et al. | |
| 2009/0305345 A1 | 12/2009 | Holliger et al. | |
| 2010/0035767 A1 | 2/2010 | Holliger et al. | |
| 2011/0301041 A1 | 12/2011 | Davidson et al. | |
| 2011/0312505 A1 | 12/2011 | Reddy et al. | |
| 2012/0308555 A1 | 12/2012 | Polakiewicz et al. | |
| 2012/0312505 A1 | 12/2012 | Youbi-Idrissi et al. | |
| 2013/0178370 A1 | 7/2013 | Lavinder et al. | |
| 2013/0295091 A1 | 11/2013 | Esslinger et al. | |
| 2014/0057799 A1 | 2/2014 | Johnson et al. | |
| 2015/0141261 A1 | 5/2015 | Hunicke-Smith et al. | |
| 2017/0088620 A1 | 3/2017 | Nioi et al. | |
| 2017/0275362 A1 | 9/2017 | Brentjens et al. | |
| 2017/0327818 A1 | 11/2017 | Ellington et al. | |
| 2018/0353603 A1 | 12/2018 | Esslinger et al. | |
| 2020/0216840 A1 | 7/2020 | Tanno et al. | |
| 2021/0130816 A1 | 5/2021 | Ellington et al. | |

FOREIGN PATENT DOCUMENTS

| | | |
|---|---|---|
| CN | 105131126 | 12/2015 |
| GB | 2502577 | 12/2013 |
| JP | 2004-81084 | 3/2004 |
| JP | 2007-505611 | 3/2007 |
| JP | 2007-319028 | 12/2007 |
| JP | 2009-284834 | 12/2009 |
| JP | 2010-535150 | 11/2010 |

(Continued)

OTHER PUBLICATIONS

Almagro & Fransson, Humanization of antibodies, Frontiers in Bioscience 2008; 13: 1619-33 (Year: 2008).*

(Continued)

*Primary Examiner* — Peter J Reddig
*Assistant Examiner* — Cheng Lu
(74) *Attorney, Agent, or Firm* — Parker Highlander PLLC

(57) ABSTRACT

Methods are provided for identifying tumor-specific antibodies and/or T-cell receptors by paired mRNA sequencing from individual immune cells in sentinel lymph nodes and comparison of these sequences with corresponding mass spectroscopy data from a subject having a cancer. Novel tumor-specific antibodies (e.g., NY-ESO-1-binding antibodies) are also provided.

11 Claims, 8 Drawing Sheets

Specification includes a Sequence Listing.

(56) References Cited

FOREIGN PATENT DOCUMENTS

| WO | WO 2016/210365 | 12/1916 |
|---|---|---|
| WO | WO 2017/044661 | 3/1917 |
| WO | WO 2017/127510 | 7/1917 |
| WO | WO 2017/173321 | 10/1917 |
| WO | WO 2018/183485 | 10/1918 |
| WO | WO 2002/022869 | 3/2002 |
| WO | WO 2003/052416 | 6/2003 |
| WO | WO 2003/060144 | 7/2003 |
| WO | WO 2004/039947 | 5/2004 |
| WO | WO 2005/042774 | 5/2005 |
| WO | WO 2005/045015 | 5/2005 |
| WO | WO 2005/045072 | 5/2005 |
| WO | WO 2005/084134 | 9/2005 |
| WO | WO 2006/037064 | 4/2006 |
| WO | WO 2006/078766 | 7/2006 |
| WO | WO 2016/176322 | 11/2006 |
| WO | WO 2008/029085 | 3/2008 |
| WO | WO 2008/050104 | 5/2008 |
| WO | WO 2008/079914 | 7/2008 |
| WO | WO 2008/104184 | 9/2008 |
| WO | WO 2009/100896 | 8/2009 |
| WO | WO 2010/062776 | 6/2010 |
| WO | WO 2010/083456 | 7/2010 |
| WO | WO 2011/146514 | 11/2011 |
| WO | WO 2012/061412 | 5/2012 |
| WO | WO 2012/072705 | 6/2012 |
| WO | WO 2012/083225 | 6/2012 |

OTHER PUBLICATIONS

Gura, T., Systems for Identifying New Drugs Are Often Faulty, Science, 1997, 278:1041-1042 (Year: 1997).*

Kaiser, J., First pass at cancer genoome reveals complex landscape, Science, 2006, 313:1370 (Year: 2006).*

Jena et al. Redirecting T-cell specificity by introducing a tumor-specific chimeric antigen receptor, Blood Aug. 19, 2010 116(7): 1035-1044 (Year: 2010).*

Arnaout, "Specificity and overlap in gene segment-defined antibody repertoires," BMC Genomics, 6:148, 2005.

Behrendt et al., "The role of somatic mutation in determining the affinity of anti-DNA antibodies," Clin Exp Immunol, 131:182-189, 2003.

Boudinot et al., "New perspectives for large-scale repertoire analysis of immune receptors," Molecular Immunology, 45:2437-2445, 2008.

Boyd et al., "Measurement and clinical monitoring of human lymphocyte clonality by massively parallel V-D-J pyrosequencing," Science Translational Medicine, 1(12):12ra23, 2009.

Burgoon et al., "Laser-capture microdissection of plasma cells from subacute sclerosing panencephalitis brain reveals intrathecal disease-relevant antibodies," PNAS, 102(20):7245-7250, 2005.

Campbell et al., "Subclonal phylogenetic structures in cancer revealed by ultra-deep sequencing," PNAS, 105(35):13081-13086, 2008.

Chandrasekaran et al., "Microenvironment of tumor-draining lymph nodes: opportunities for liposome-based targeted therapy," Int J Mol Sci, 15(11):20209-39, 2014.

Chapal et al., "Thyroid peroxidase autoantibodies obtained from random single chain Fv libraries contain the same heavy/light chain combinations as occur in vivo," Endocrinology, 142(11):4740-4750, 2001.

Cheung et al., "A proteomics approach for the identification and cloning of monoclonal antibodies from serum," Nature Biotechnology, 30(5):447-52, 2012.

Clackson et al., "Making antibody fragments using phage display libraries," Letters to Nature, 352:624-628, 1991.

Correia-Neves et al., "The shaping of the T cell repertoire," Immunity, 14:21-32, 2001.

Damoc et al., "High resolution proteome analysis of cryoglobulins using Fourier transform-ion cyclotron resonance mass spectrometry," Proteomics, 3:1425-1433, 2003.

De Costa et al., "Sequencing and quantifying IgG fragments and antigen-binding regions by mass spectrometiy," Journal of Proteome Research, 9:2937-2945, 2010.

DeKosky et al., "High-throughput sequencing of the paired human immunoglobulin heavy and light chain repertoire," Nature Biotechnology, 31(2):166-169, 2013.

DeKosky et al., "In-depth determination and analysis of the human paired heavy-and light-chain antibody repertoire," Nature Medicine, 21.1: 86-91, 2015.

DeKosky et al., "Large-scale sequence and structural comparisons of human naive and antigen-experienced antibody repertoires," Proceedings of the National Academy of Sciences, 113.19: E2636-E2645, 2016.

Devarakonda et al., "Patient-derived heavy chain antibody targets cell surface HSP90 on breast tumors," BMC Cancer, 15:614, 2015.

Dornmair et al., "Novel approaches for identifying target antigens of autoreactive human B and T cells," Seminars in Immunopathology, 31(4):467-477, 2009.

Ellefson et al., "Synthetic evolutionary origin of a proofreading reverse transcriptase," Science, 352: 1590-1593, 2016.

Ellefson et al., "Synthetic evolutionary origin of a proofreading reverse transcriptase," Science, 352: 1590-1593, 2016. Supplementary Materials.

Elshawadfy et al., "DNA polymerase hybrids derived from the family-B enzymes of Pyrococcus furiosus and Thermococcus kodakarensis: improving performance in the polymerase chain reaction," Front. Microbiol., 5(244):1-14, 2014.

Fischer et al., "Sequencing antibody repertoires: the next generation," MAbs, 3(1):17-20, 2011.

Freeman et al., "Profiling the T-cell receptor beta-chain repertoire by massively parallel sequencing," Genome Research, 19:1817-1824, 2009.

Georgiou et al., "The promise and challenge of high-throughput sequencing of the antibody repertoire," Nature Biotechnology, 32.2: 158-168, 2014.

Glanville et al., "Precise determination of the diversity of a combinatorial antibody library gives insight into the human immunoglobulin repertoire," Proc Natl Acad Sci USA, 106(48):20216-20221, 2009.

Huse et al., "Purification of antibodies by affinity chromatography," J Biochem Biophys Methods, 51:217-231, 2002.

Instructions for Product Nos. 21901 and 21902, Maleimide-PEG2-Biotin Sulfhydryl-reactive biotin labeling reagent with polyethylene glycol (PEG) spacer arm, published by Thermo Fisher Scientific, Inc., 2008.

International Preliminary Report on Patentability issued in corresponding PCT Application No. PCT/US2018/057961, dated May 7, 2020.

International Search Report and Written Opinion issued in corresponding PCT Application No. PCT/US2018/057961, dated Feb. 11, 2019.

Ippolito et al., "Antibody repertoires in humanized NOD-scid-IL2Rγ(null) mice and human B cells reveals human-like diversification and tolerance checkpoints in the mouse," PLoS One, 7(4):e35497, 2012.

Kumaresan et al., "High-throughput single copy DNA amplification and cell analysis in engineered nanoliter droplets," Analytical Chemistry, 80 (10):3522-3529, 2008.

Kurokawa et al., "Paired cloning of the T cell receptor α and β genes from a single T cell without the establishment of a T cell clone," Clin Exp Immunol, 123:340-345, 2001.

Lavinder et al., "Next-generation sequencing and protein mass spectrometry for the comprehensive analysis of human cellular and serum antibody repertoires," Curr Opin Chem Biol, 24:112-20, 2015.

Maiolica et al., "Targeted proteome investigation via selected reaction monitoring mass spectrometry," Journal of Proteomics, 75(12):3495-3513, 2012.

Maksimov et al., "Analysis of clonal type-specific antibody reactions in Toxoplasma gondii seropositive humans from Germany by peptide-microarray," PLoS One, 7(3):e34212., 2012.

Mary et al., "Analysis of gene expression at the single-cell level using microdroplet-based microfluidic technology," Biomicrofluidics, 5:024109, 2011.

(56) References Cited

OTHER PUBLICATIONS

Matsutani et al., "Restricted usage of T-cell receptor α-chain variable region (TCRAV) and T-cell receptor β-chain variable region (TCRBV) repertoires after human allogeneic haematopoietic transplantation," British Journal of Haematology, 109:759-769, 2000.

McDaniel et al. "Mapping the secrets of the antibody pool," Nat Biotechnol, 35(10):921-922, 2017.

McDaniel et al., "Identification of tumor-reactive B cells and systemic IgG in breast cancer based on clonal frequency in the sentinel lymph node," Cancer Immunol Immunother, 67(5):729-738, 2018.

McDaniel et al., "Ultra-high-throughput sequencing of the immune receptor repertoire from millions of lymphocytes," Nature Protocols, 11.3: 429-442, 2016.

McMahan et al., "Production, characterization, and immunogenicity of a soluble rat single chain T cell receptor specific for an encephalitogenic peptide," The Journal of Biological Chemistry, 278(33):30961-30970, 2003.

Meijer et al., "Isolation of human antibody repertoires with preservation of the natural heavy and light chain pairing," Journal of Molecular Biology, 358(3): 764-772, 2006.

Meijer et al., "Isolation of human antibody repertoires with preservation of the natural heavy and light chain pairing," Journal of Molecular Biology, 358(3): 764-772, 2006. (Supplementary Data).

Mouquet et al., "Complex-type N-glycan recognition by potent broadly neutralizing HIV antibodies," Proc Natl Acad Sci USA, 109(47):E3268-E3277, 2012.

Nazabal et al., "Immunoassays with direct mass spectrometric detection," Analytical Chemistry, 78(11):3562-3570, 2006.

Nishioka et al., "Long and accurate PCR with a mixture of KOD DNA polymerase and its exonuclease deficient mutant enzyme," Journal of Biotechnology, 88: 141-149, 2001.

Novak et al., "Single-cell multiplex gene detection and sequencing with microfluidically generated agarose emulsions," Angew. Chem. Int. Ed., 50:390-395, 2011.

Obermeier et al., "Matching of oligoclonal immunoglobulin transcriptomes and proteomes of cerebrospinal fluid in multiple sclerosis," Nature Medicine, 14(6):688-693, 2008.

Omenn et al., "Overview of the HUPO plasma proteome project: results from the pilot phase with 35 collaborating laboratories and multiple analytical groups, generating a core dataset of 3020 proteins and a publicly-available database", Proteomics, 5:3226-3245, 2005. [Supplementary Materials, Protein dataset].

Packer and Muraro, "Optimized clonotypic analysis of T-cell receptor repertoire in immune reconstitution," Experimental Hematology, 35:516-521, 2007.

Peng, "Protein mixture analysis by tandem mass spectrometry" In: The Bioinformatics of Brains: From Genes and Proteins to Behaviors (Williams RW, ed.), pp. 61-68 (2003), Washington, DC: Society for Neuroscience.

Persson et al., "Generation of diverse high-affinity human monoclonal antibodies by repertoire cloning," Proc. Natl. Acad. Sci. USA, 88:2432-2436, 1991.

Ravetch et al., "Structure of the human immunoglobulin mu locus: characterization of embryonic and rearranged J and D genes", Cell, 27:583-591, 1981.

Reddy et al., "Monoclonal antibodies isolated without screening by analyzing the variable-gene repertoire of plasma cells", Nature Biotechnology, 28(9):965-9, 2010.

Rodriguez-Pinto et al., "Identification of novel tumor antigens with patient-derived immune-selected antibodies", Cancer Immunol Immunother, 58(2):221-34, 2009.

Rothe et al., "Construction of phage display libraries from reactive lymph nodes of breast carcinoma patients and selection for specifically binding human single chain Fv on cell lines," Int J Mol Med, 14(4):729-35, 2004.

Sano et al., "Mutations to create thermostable reverse transcriptase with bacterial family A DNA polymerase from Thermotoga petrophila K4," Journal of Bioscience and Bioengineering, 113.3: 315-321, 2012.

Sato et al., "Proteomics-directed cloning of circulating antiviral human monoclonal antibodies," Nature Biotechnology, 30(11):1039-1043, 2012.

Schluter et al., "Sequence analysis of homogeneous peptides of shark immunoglobulin light chains by tandem mass spectrometry: correlation with gene sequence and homologies among variable and constant region peptides of sharks and mammals," Molecular Immunology, 27(1):17-23, 1990.

Tanaka et al., "Single-cell analysis of T-cell receptor repertoire of HTLV-1 tax-specific cytotoxic T-cells in allogeneic transplant recipients with adult T-cell leukemia/lymphoma," Cancer Research, 70(15): 6181-6192, 2010.

Tanno et al., "A facile technology for the high-throughput sequencing of the paired VH: VL and TCRβ: TCRα repertoires," Science Advances 6.17: eaay9093, 2020.

Wang et al., "Functional interrogation and mining of natively paired human V H: V L antibody repertoires," Nature Biotechnology 36.2: 152, 2018.

Weinstein et al., "High-throughput sequencing of the zebrafish antibody repertoire," Science, 324:807-810, 2009.

Willis et al., "Rapid molecular cloning of rearrangements of the IGHJ locus using long-distance inverse polymerase chain reaction," Blood, 90(6):2456-2464, 1997.

Wine et al., "Molecular deconvolution of the monoclonal antibodies that comprise the polyclonal serum response," Proc Natl Acad Sci USA, 110(8):2993-2998, 2013.

Yates, "Mass spectrometry from genomics to proteomics," Trends Genet., 16(1):5-8, 2000.

Zhang et al., "Massively parallel single-molecule and single-cell emulsion reverse transcription polymerase chain reaction using agarose droplet microfluidics," Analytical Chemistry, 84:3599-3605, 2012.

\* cited by examiner

B. VH:VL pairing specificity for BC2-3G

| | CDR-H3 | VH | JH | CDR-L3 | VL | JL | $K_D$ (nM) |
|---|---|---|---|---|---|---|---|
| 1 | CARDLGIAAAGDFDYW | VH6-1 | JH4 | CQQGSNWPTF | VK3-11 | JK4 | 37 ± 9 |
| 2 | CARDLGPAAAADFDYW | VH6-1 | JH4 | CQQHFNWPTF | VK3-11 | JK4 | 17.4 ± 2.2 |
| 3 | CARDLGVTAAADFDFW | VH6-1 | JH4 | CQQHFNWPTF | VK3-11 | JK4 | 6.2 ± 1.7 |
| 4 | CARDLGLAAAADFDFW | VH6-1 | JH4 | CQQHRSWPTF | VK3-11 | JK4 | 2.0 ± 0.2 |

C. Representative heavy chain members of BC2-3G lineage (VH6-1)

```
  QVQLQQSGPGLVKPSQTLSLTCAISGDSVSSNSAAWNWIRQSPSRGLEWLGRIYYRSKWYN
1 ············································································
2 ···········································································S
3 ···········································································S
4 ·······················N············T································R··H

DYAVSVKSRITINPDTSKNQFSLQLNSVTPEDTAVYYCARDLGIAAAGYFDYWGQGTLVTVSS
1 ·········································D··················
2 ··················V······················P···AD··············
3 ·······T··········L··H·K··················VT··AD··F···········
4 ···L·······S················S·····I·······L···AD··F·········I···
```

D. Representative paired light chains mapping to BC2-3G lineage (VK3-11)

```
  EIVLTQSPATLSLSPGERATLSCRASQGVSSYLAWYQQKPGQAPRLLIYDAS
1 ····················································
2 ·······························S·················S···
3 ·······························S·················S···
4 ···M····V······················S······················

NRATGIPARFSGSGPGTDFTLTISSLEPEDFAVYYCQQRSNWLTFGGGTKVEI
1 ··············S···················H·G··P···········
2 ··············S·N·················F··H·HF··P········
3 ··············S·N·················F··H·HF··P········
4 K·············S···················H·HRS·P···········
```

FIGS. 2B-D

F. Peptides detected from BC2-3G sub-lineage 1

QVQLQQSGPGLVKPSQTLSLTCAISGDSVSSNSAAWNWIRQSPSRGLEWLGRTYYRSKWYNDYAVSVK
SRITINPDTSKNQFSLQLNSVTPEDTAVYYCARDLGIAAAGDFDYWGQGTLVTVSSASTK

A. Phylogenetic analysis of lineage BC2-4G

B. VH:VL pairing specificity for BC2-4G

|   | CDR-H3 | VH | JH | CDR-L3 | VL | JL |
|---|---|---|---|---|---|---|
| 1 | CARHGLGWDLYYFDYW | VH4-59 | JH4 | CQSYDSSLIGYVF | VL1-40 | JL1 |
| 2 | CARHGSGWDLYYFDYW | VH4-59 | JH4 | CQSYDASLKGYVF | VL1-40 | JL1 |

C. Representative heavy chain members of BC2-4G lineage (VH4-59)

```
  QVQLQESGPGLVKPSETLSLTCTVSGGSISSYYWSWIRQPPGKGLEWIGYIYYSGSINYN
1 ·····························TN······················N·EN·
2 ····Q························N························N·N·D··

PSLKSRVTISVDTSKNQFSLKLSSVTAADTAVYYCARHGLGWDLYYFDYWGQGTLVPVSS
1 ············································································
2 S······M···S······T·K·M············S················I··TA··
```

D. Representative paired light chains mapping to BC2-4G lineage (VL1-40)

```
  QSVLTQPPSVSGAPGQRVTISCTGSSSNIGAGYDVHWYQQLPGTAPKLLIYGNS
1 ····················································T
2 ·················T·L········Q··················S·N

NRPSGVPDRFSGSKSGTSASLAITGLQAEDEADYYCQSYDSSLSGYVFGTGTKVTV
1 ································I···········S·
2 ································A··K····P······
```

FIGS. 3B-D

```
SEQUENCE LISTING

<160> NUMBER OF SEQ ID NOS: 140

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

Gly Asp Ser Val Ser Ser Asn Ser Ala Ala
1               5                   10

<210> SEQ ID NO 2
<211> LENGTH: 10
<212> TYPE: PRT
<213> ORGANISM: Artificial sequence
<220> FEATURE:
<223> OTHER INFORMATION: Synthetic peptide

<400> SEQUENCE: 2

Gly Asp Ser Val Ser Ser Asn Thr Ala Ala
1               5                   10

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Thr Tyr Tyr Arg Ser Lys Trp Tyr Asn
1               5
```

```
<210> SEQ ID NO 4
<211> LENGTH: 9
<212> TYPE: PRT
<213> ORGANISM: Artificial sequence
<220> FEATURE:
<223> OTHER INFORMATION: Synthetic peptide

<400> SEQUENCE: 4

Thr Tyr Tyr Arg Ser Lys Trp Tyr Ser
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Thr Tyr Tyr Arg Ser Arg Trp Tyr His
1               5

<210> SEQ ID NO 6
<211> LENGTH: 16
<212> TYPE: PRT
<213> ORGANISM: Artificial sequence
<220> FEATURE:
<223> OTHER INFORMATION: Synthetic peptide

<400> SEQUENCE: 6

Cys Ala Arg Asp Leu Gly Ile Ala Ala Ala Gly Asp Phe Asp Tyr Trp
1               5                   10                  15

<210> SEQ ID NO 7
<211> LENGTH: 16
<212> TYPE: PRT
<213> ORGANISM: Artificial sequence
<220> FEATURE:
<223> OTHER INFORMATION: Synthetic peptide

<400> SEQUENCE: 7

Cys Ala Arg Asp Leu Gly Pro Ala Ala Ala Ala Asp Phe Asp Tyr Trp
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: Synthetic peptide

<400> SEQUENCE: 8

Cys Ala Arg Asp Leu Gly Val Thr Ala Ala Ala Asp Phe Asp Phe Trp
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: Synthetic peptide

<400> SEQUENCE: 9

Cys Ala Arg Asp Leu Gly Leu Ala Ala Ala Ala Asp Phe Asp Phe Trp
1               5                   10                  15
```

```
<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Gln Gly Val Ser Ser Tyr
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Gln Ser Val Ser Ser Tyr
1               5

<210> SEQ ID NO 12
<211> LENGTH: 3
<212> TYPE: PRT
<213> ORGANISM: Artificial sequence
<220> FEATURE:
<223> OTHER INFORMATION: Synthetic peptide

<400> SEQUENCE: 12

Asp Ala Ser
1

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13

Cys His Gln Gly Ser Asn Trp Pro Thr Phe
1               5                   10

<210> SEQ ID NO 14
<211> LENGTH: 10
<212> TYPE: PRT
<213> ORGANISM: Artificial sequence
<220> FEATURE:
<223> OTHER INFORMATION: Synthetic peptide

<400> SEQUENCE: 14

Cys His Gln His Phe Asn Trp Pro Thr Phe
1               5                   10

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15

Cys His Gln His Arg Ser Trp Pro Thr Phe
1               5                   10
```

```
<210> SEQ ID NO 16
<211> LENGTH: 16
<212> TYPE: PRT
<213> ORGANISM: Artificial sequence
<220> FEATURE:
<223> OTHER INFORMATION: Synthetic peptide

<400> SEQUENCE: 16

Cys Ala Arg Asp Leu Gly Ile Ala Ala Ala Gly Tyr Phe Asp Tyr Trp
1               5                   10                  15

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Cys Gln Gln Arg Ser Asn Trp Leu Thr Phe
1               5                   10

<210> SEQ ID NO 18
<211> LENGTH: 7
<212> TYPE: PRT
<213> ORGANISM: Artificial sequence
<220> FEATURE:
<223> OTHER INFORMATION: Synthetic peptide

<400> SEQUENCE: 18

Gly Gly Ser Ile Ser Ser Tyr
1               5

<210> SEQ ID NO 19
<211> LENGTH: 7
<212> TYPE: PRT
<213> ORGANISM: Artificial sequence
<220> FEATURE:
<223> OTHER INFORMATION: Synthetic peptide

<400> SEQUENCE: 19

Gly Gly Ser Ile Thr Asn Tyr
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic peptide

<400> SEQUENCE: 20

Gly Gly Ser Ile Ser Asn Tyr
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic peptide

<400> SEQUENCE: 21

Ile Tyr Tyr Ser Gly Ser Thr
1               5
```

```
<210> SEQ ID NO 22
<211> LENGTH: 7
<212> TYPE: PRT
<213> ORGANISM: Artificial sequence
<220> FEATURE:
<223> OTHER INFORMATION: Synthetic peptide

<400> SEQUENCE: 22

Ile Tyr Tyr Ser Gly Asn Thr
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic peptide

<400> SEQUENCE: 23

Ile Tyr Tyr Asn Gly Asn Thr
1               5

<210> SEQ ID NO 24
<211> LENGTH: 16
<212> TYPE: PRT
<213> ORGANISM: Artificial sequence
<220> FEATURE:
<223> OTHER INFORMATION: Synthetic peptide

<400> SEQUENCE: 24

Cys Ala Arg His Gly Leu Gly Trp Asp Leu Tyr Tyr Phe Asp Tyr Trp
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: Synthetic peptide

<400> SEQUENCE: 25

Cys Ala Arg His Gly Ser Gly Trp Asp Leu Tyr Tyr Phe Asp Tyr Trp
1               5                   10                  15

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Ser Ser Asn Ile Gly Ala Gly Tyr Asp
1               5

<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Ser Leu Asn Ile Gly Ala Gly Tyr Asp
1               5
```

-continued

```
<210> SEQ ID NO 28
<211> LENGTH: 3
<212> TYPE: PRT
<213> ORGANISM: Artificial sequence
<220> FEATURE:
<223> OTHER INFORMATION: Synthetic peptide

<400> SEQUENCE: 28

Gly Asn Ser
1

<210> SEQ ID NO 29
<211> LENGTH: 3
<212> TYPE: PRT
<213> ORGANISM: Artificial sequence
<220> FEATURE:
<223> OTHER INFORMATION: Synthetic peptide

<400> SEQUENCE: 29

Gly Asn Thr
1

<210> SEQ ID NO 30
<211> LENGTH: 3
<212> TYPE: PRT
<213> ORGANISM: Artificial sequence
<220> FEATURE:
<223> OTHER INFORMATION: Synthetic peptide

<400> SEQUENCE: 30

Ser Asn Asn
1

<210> SEQ ID NO 31
<211> LENGTH: 13
<212> TYPE: PRT
<213> ORGANISM: Artificial sequence
<220> FEATURE:
<223> OTHER INFORMATION: Synthetic peptide

<400> SEQUENCE: 31

Cys Gln Ser Tyr Asp Ser Ser Leu Ser Gly Tyr Val Phe
1               5                   10

<210> SEQ ID NO 32
<211> LENGTH: 13
<212> TYPE: PRT
<213> ORGANISM: Artificial sequence
<220> FEATURE:
<223> OTHER INFORMATION: Synthetic peptide

<400> SEQUENCE: 32

Cys Gln Ser Tyr Asp Ser Ser Leu Ile Gly Tyr Val Phe
1               5                   10

<210> SEQ ID NO 33
<211> LENGTH: 13
<212> TYPE: PRT
<213> ORGANISM: Artificial sequence
<220> FEATURE:
<223> OTHER INFORMATION: Synthetic peptide

<400> SEQUENCE: 33

Cys Gln Ser Tyr Asp Ala Ser Leu Lys Gly Tyr Val Phe
1               5                   10
```

-continued

```
<210> SEQ ID NO 34
<211> LENGTH: 8
<212> TYPE: PRT
<213> ORGANISM: Artificial sequence
<220> FEATURE:
<223> OTHER INFORMATION: Synthetic peptide

<400> SEQUENCE: 34

Gly Gly Thr Phe Ser Ser Tyr Ala
1               5

<210> SEQ ID NO 35
<211> LENGTH: 8
<212> TYPE: PRT
<213> ORGANISM: Artificial sequence
<220> FEATURE:
<223> OTHER INFORMATION: Synthetic peptide

<400> SEQUENCE: 35

Ile Ile Pro Ile Leu Gly Ile Ala
1               5

<210> SEQ ID NO 36
<211> LENGTH: 8
<212> TYPE: PRT
<213> ORGANISM: Artificial sequence
<220> FEATURE:
<223> OTHER INFORMATION: Synthetic peptide

<400> SEQUENCE: 36

Ile Ile Pro Ile Leu Gly Val Thr
1               5

<210> SEQ ID NO 37
<211> LENGTH: 9
<212> TYPE: PRT
<213> ORGANISM: Artificial sequence
<220> FEATURE:
<223> OTHER INFORMATION: Synthetic peptide

<400> SEQUENCE: 37

Cys Ala Ser Val Thr Ser Gly Tyr Trp
1               5

<210> SEQ ID NO 38
<211> LENGTH: 7
<212> TYPE: PRT
<213> ORGANISM: Artificial sequence
<220> FEATURE:
<223> OTHER INFORMATION: Synthetic peptide

<400> SEQUENCE: 38

Gln Ser Val Ser Ser Ser Ser
1               5

<210> SEQ ID NO 39
<211> LENGTH: 7
<212> TYPE: PRT
<213> ORGANISM: Artificial sequence
<220> FEATURE:
<223> OTHER INFORMATION: Synthetic peptide

<400> SEQUENCE: 39

Gln Ser Ile Ser Ser Ser Tyr
1               5
```

```
<210> SEQ ID NO 40
<211> LENGTH: 3
<212> TYPE: PRT
<213> ORGANISM: Artificial sequence
<220> FEATURE:
<223> OTHER INFORMATION: Synthetic peptide

<400> SEQUENCE: 40

Gly Ala Ser
1

<210> SEQ ID NO 41
<211> LENGTH: 3
<212> TYPE: PRT
<213> ORGANISM: Artificial sequence
<220> FEATURE:
<223> OTHER INFORMATION: Synthetic peptide

<400> SEQUENCE: 41

Ser Ala Ser
1

<210> SEQ ID NO 42
<211> LENGTH: 14
<212> TYPE: PRT
<213> ORGANISM: Artificial sequence
<220> FEATURE:
<223> OTHER INFORMATION: Synthetic peptide

<400> SEQUENCE: 42

Cys Gln Gln His Gly Ile Ser Pro Pro Phe Met Tyr Thr Phe
1               5                   10

<210> SEQ ID NO 43
<211> LENGTH: 14
<212> TYPE: PRT
<213> ORGANISM: Artificial sequence
<220> FEATURE:
<223> OTHER INFORMATION: Synthetic peptide

<400> SEQUENCE: 43

Cys Gln His Tyr Gly Ser Ser Pro Ala Phe Met Tyr Thr Phe
1               5                   10

<210> SEQ ID NO 44
<211> LENGTH: 9
<212> TYPE: PRT
<213> ORGANISM: Artificial sequence
<220> FEATURE:
<223> OTHER INFORMATION: Synthetic peptide

<400> SEQUENCE: 44

Cys Ala Ser Val Thr Ser Arg Tyr Trp
1               5

<210> SEQ ID NO 45
<211> LENGTH: 19
<212> TYPE: DNA
<213> ORGANISM: Artificial sequence
<220> FEATURE:
<223> OTHER INFORMATION: Synthetic primer

<400> SEQUENCE: 45
cgcagtagcg gtaaacggc                                                  19
```

```
<210> SEQ ID NO 46
<211> LENGTH: 22
<212> TYPE: DNA
<213> ORGANISM: Artificial sequence
<220> FEATURE:
<223> OTHER INFORMATION: Synthetic primer

<400> SEQUENCE: 46
gcggataaca atttcacaca gg                                            22

<210> SEQ ID NO 47
<211> LENGTH: 40
<212> TYPE: DNA
<213> ORGANISM: Artificial sequence
<220> FEATURE:
<223> OTHER INFORMATION: Synthetic primer

<400> SEQUENCE: 47
tattcccatc gcggcgccag gtccagctkg trcagtctgg                         40

<210> SEQ ID NO 48
<211> LENGTH: 40
<212> TYPE: DNA
<213> ORGANISM: Artificial sequence
<220> FEATURE:
<223> OTHER INFORMATION: Synthetic primer

<400> SEQUENCE: 48
tattcccatc gcggcgccag gtgcagctgg tgsartctgg                         40

<210> SEQ ID NO 49
<211> LENGTH: 39
<212> TYPE: DNA
<213> ORGANISM: Artificial sequence
<220> FEATURE:
<223> OTHER INFORMATION: Synthetic primer

<400> SEQUENCE: 49
tattcccatc gcggcgccag rtcaccttga aggagtctg                          39

<210> SEQ ID NO 50
<211> LENGTH: 38
<212> TYPE: DNA
<213> ORGANISM: Artificial sequence
<220> FEATURE:
<223> OTHER INFORMATION: Synthetic primer

<400> SEQUENCE: 50
tattcccatc gcggcgcgag gtgcagctgk tggagwcy                           38

<210> SEQ ID NO 51
<211> LENGTH: 39
<212> TYPE: DNA
<213> ORGANISM: Artificial sequence
<220> FEATURE:
<223> OTHER INFORMATION: Synthetic primer

<400> SEQUENCE: 51
tattcccatc gcggcgccag gtgcagctgc aggagtcsg                          39

<210> SEQ ID NO 52
<211> LENGTH: 39
<212> TYPE: DNA
<213> ORGANISM: Artificial sequence
<220> FEATURE:
<223> OTHER INFORMATION: Synthetic primer
```

<400> SEQUENCE: 52
tattcccatc gcggcgccag gtgcagctac agcagtggg        39

<210> SEQ ID NO 53
<211> LENGTH: 38
<212> TYPE: DNA
<213> ORGANISM: Artificial sequence
<220> FEATURE:
<223> OTHER INFORMATION: Synthetic primer

<400> SEQUENCE: 53
tattcccatc gcggcgccag gtacagctgc agcagtca        38

<210> SEQ ID NO 54
<211> LENGTH: 39
<212> TYPE: DNA
<213> ORGANISM: Artificial sequence
<220> FEATURE:
<223> OTHER INFORMATION: Synthetic primer

<400> SEQUENCE: 54
tattcccatc gcggcgctca acacaacggt tcccagtta        39

<210> SEQ ID NO 55
<211> LENGTH: 47
<212> TYPE: DNA
<213> ORGANISM: Artificial sequence
<220> FEATURE:
<223> OTHER INFORMATION: Synthetic primer

<400> SEQUENCE: 55
gcgccgcgat gggaatagct agccgacatc crgdtgaccc agtctcc        47

<210> SEQ ID NO 56
<211> LENGTH: 47
<212> TYPE: DNA
<213> ORGANISM: Artificial sequence
<220> FEATURE:
<223> OTHER INFORMATION: Synthetic primer

<400> SEQUENCE: 56
gcgccgcgat gggaatagct agccgatatt gtgmtgacbc agwctcc        47

<210> SEQ ID NO 57
<211> LENGTH: 47
<212> TYPE: DNA
<213> ORGANISM: Artificial sequence
<220> FEATURE:
<223> OTHER INFORMATION: Synthetic primer

<400> SEQUENCE: 57
gcgccgcgat gggaatagct agccgaaatt gtrwtgacrc agtctcc        47

<210> SEQ ID NO 58
<211> LENGTH: 46
<212> TYPE: DNA
<213> ORGANISM: Artificial sequence
<220> FEATURE:
<223> OTHER INFORMATION: Synthetic primer

<400> SEQUENCE: 58
gcgccgcgat gggaatagct agccgaaacg acactcacgc agtctc        46

-continued

```
<210> SEQ ID NO 59
<211> LENGTH: 47
<212> TYPE: DNA
<213> ORGANISM: Artificial sequence
<220> FEATURE:
<223> OTHER INFORMATION: Synthetic primer

<400> SEQUENCE: 59
gcgccgcgat gggaatagct agcccagtct gtsbtgacgc agccgcc         47

<210> SEQ ID NO 60
<211> LENGTH: 44
<212> TYPE: DNA
<213> ORGANISM: Artificial sequence
<220> FEATURE:
<223> OTHER INFORMATION: Synthetic primer

<400> SEQUENCE: 60
gcgccgcgat gggaatagct agcccagcct gtgctgactc aryc            44

<210> SEQ ID NO 61
<211> LENGTH: 47
<212> TYPE: DNA
<213> ORGANISM: Artificial sequence
<220> FEATURE:
<223> OTHER INFORMATION: Synthetic primer

<400> SEQUENCE: 61
gcgccgcgat gggaatagct agcccagccw gkgctgactc agccmcc         47

<210> SEQ ID NO 62
<211> LENGTH: 45
<212> TYPE: DNA
<213> ORGANISM: Artificial sequence
<220> FEATURE:
<223> OTHER INFORMATION: Synthetic primer

<400> SEQUENCE: 62
gcgccgcgat gggaatagct agcccagtct gyyctgaytc agcct           45

<210> SEQ ID NO 63
<211> LENGTH: 46
<212> TYPE: DNA
<213> ORGANISM: Artificial sequence
<220> FEATURE:
<223> OTHER INFORMATION: Synthetic primer

<400> SEQUENCE: 63
gcgccgcgat gggaatagct agcctcctat gwgctgacwc agccaa          46

<210> SEQ ID NO 64
<211> LENGTH: 47
<212> TYPE: DNA
<213> ORGANISM: Artificial sequence
<220> FEATURE:
<223> OTHER INFORMATION: Synthetic primer

<400> SEQUENCE: 64
gcgccgcgat gggaatagct agcctcctct gagctgastc aggascc         47

<210> SEQ ID NO 65
<211> LENGTH: 47
<212> TYPE: DNA
<213> ORGANISM: Artificial sequence
<220> FEATURE:
<223> OTHER INFORMATION: Synthetic primer
```

```
<400> SEQUENCE: 65
gcgccgcgat gggaatagct agcctcctat gagctgayrc agcyacc                47

<210> SEQ ID NO 66
<211> LENGTH: 46
<212> TYPE: DNA
<213> ORGANISM: Artificial sequence
<220> FEATURE:
<223> OTHER INFORMATION: Synthetic primer

<400> SEQUENCE: 66
gcgccgcgat gggaatagct agccaatttt atgctgactc agcccc                 46

<210> SEQ ID NO 67
<211> LENGTH: 47
<212> TYPE: DNA
<213> ORGANISM: Artificial sequence
<220> FEATURE:
<223> OTHER INFORMATION: Synthetic primer

<400> SEQUENCE: 67
gcgccgcgat gggaatagct agcccagdct gtggtgacyc aggagcc                47

<210> SEQ ID NO 68
<211> LENGTH: 53
<212> TYPE: DNA
<213> ORGANISM: Artificial sequence
<220> FEATURE:
<223> OTHER INFORMATION: Synthetic primer

<400> SEQUENCE: 68
cgcagtagcg gtaaacggcc gacggggaat tctcacagga gacgaggggg aaa         53

<210> SEQ ID NO 69
<211> LENGTH: 43
<212> TYPE: DNA
<213> ORGANISM: Artificial sequence
<220> FEATURE:
<223> OTHER INFORMATION: Synthetic primer

<400> SEQUENCE: 69
cgcagtagcg gtaaacggcg gagsagggyg ccaggggaa gac                     43

<210> SEQ ID NO 70
<211> LENGTH: 45
<212> TYPE: DNA
<213> ORGANISM: Artificial sequence
<220> FEATURE:
<223> OTHER INFORMATION: Synthetic primer

<400> SEQUENCE: 70
cgcagtagcg gtaaacggcg ctcagcggga agaccttggg gctgg                  45

<210> SEQ ID NO 71
<211> LENGTH: 49
<212> TYPE: DNA
<213> ORGANISM: Artificial sequence
<220> FEATURE:
<223> OTHER INFORMATION: Synthetic primer

<400> SEQUENCE: 71
gcggataaca atttcacaca ggttgragct cctcagagga gggygggaa              49
```

-continued

```
<210> SEQ ID NO 72
<211> LENGTH: 63
<212> TYPE: DNA
<213> ORGANISM: Artificial sequence
<220> FEATURE:
<223> OTHER INFORMATION: Synthetic primer

<400> SEQUENCE: 72
gcggataaca atttcacaca ggctgctcat cagatggcgg gaagatgaag acagatggtg    60
cag                                                                 63

<210> SEQ ID NO 73
<211> LENGTH: 31
<212> TYPE: DNA
<213> ORGANISM: Artificial sequence
<220> FEATURE:
<223> OTHER INFORMATION: Synthetic primer

<400> SEQUENCE: 73
atgggccctg sgatgggccc ttggtggarg c                                   31

<210> SEQ ID NO 74
<211> LENGTH: 30
<212> TYPE: DNA
<213> ORGANISM: Artificial sequence
<220> FEATURE:
<223> OTHER INFORMATION: Synthetic primer

<400> SEQUENCE: 74
atgggccctg ggttggggcg gatgcactcc                                     30

<210> SEQ ID NO 75
<211> LENGTH: 30
<212> TYPE: DNA
<213> ORGANISM: Artificial sequence
<220> FEATURE:
<223> OTHER INFORMATION: Synthetic primer

<400> SEQUENCE: 75
atgggccctg cttggggctg gtcggggatg                                     30

<210> SEQ ID NO 76
<211> LENGTH: 30
<212> TYPE: DNA
<213> ORGANISM: Artificial sequence
<220> FEATURE:
<223> OTHER INFORMATION: Synthetic primer

<400> SEQUENCE: 76
gtgcggccgc agatggtgca gccacagttc                                     30

<210> SEQ ID NO 77
<211> LENGTH: 30
<212> TYPE: DNA
<213> ORGANISM: Artificial sequence
<220> FEATURE:
<223> OTHER INFORMATION: Synthetic primer

<400> SEQUENCE: 77
gtgcggccgc gagggyggga acagagtgac                                     30

<210> SEQ ID NO 78
<211> LENGTH: 124
<212> TYPE: PRT
<213> ORGANISM: Artificial sequence
```

```
<220> FEATURE:
<223> OTHER INFORMATION: Synthetic peptide

<400> SEQUENCE: 78

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Leu Gly Ile Ala Ala Ala Gly Tyr Phe Asp
            100                 105                 110

Tyr Trp Gly Gln Gly Thr Leu Val Thr Val Ser Ser
            115                 120

<210> SEQ ID NO 79
<211> LENGTH: 105
<212> TYPE: PRT
<213> ORGANISM: Artificial sequence
<220> FEATURE:
<223> OTHER INFORMATION: Synthetic peptide

<400> SEQUENCE: 79

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Gly Ser Asn Trp Leu Thr
                85                  90                  95

Phe Gly Gly Gly Thr Lys Val Glu Ile
            100                 105

<210> SEQ ID NO 80
<211> LENGTH: 127
<212> TYPE: PRT
<213> ORGANISM: Artificial sequence
<220> FEATURE:
<223> OTHER INFORMATION: Synthetic peptide

<400> SEQUENCE: 80

Gln Val Gln Leu Gln Gln Ser Gly Pro Gly Leu Val Lys Pro Ser Gln
1               5                   10                  15

Thr Leu Ser Thr Cys Ala Ile Ser Gly Asp Ser Val Ser Ser Asn Ser
            20                  25                  30

Ala Ala Trp Asn Trp Ile Arg Gln Ser Pro Ser Arg Gly Leu Glu Trp
        35                  40                  45
```

Leu Gly Arg Thr Tyr Tyr Arg Ser Lys Trp Tyr Asn Asp Tyr Ala Val
    50                  55                  60

Ser Val Lys Ser Arg Ile Thr Ile Asn Pro Asp Thr Ser Lys Asn Gln
65                  70                  75                  80

Phe Ser Leu Gln Leu Asn Ser Val Thr Pro Glu Asp Thr Ala Val Tyr
                85                  90                  95

Tyr Cys Ala Arg Asp Leu Gly Ile Ala Ala Ala Gly Asp Phe Asp Thr
            100                 105                 110

Trp Gly Gln Gly Thr Leu Val Thr Val Ser Ser Ala Ser Thr Lys
            115                 120                 125

<210> SEQ ID NO 81
<211> LENGTH: 116
<212> TYPE: PRT
<213> ORGANISM: Artificial sequence
<220> FEATURE:
<223> OTHER INFORMATION: Synthetic peptide

<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ile Ser Tyr Tyr
            20                  25                  30

Trp Ser Trp Ile Arg Gln Pro Pro Gly Lys Gly Leu Glu Trp Ile Gly
        35                  40                  45

Ile Tyr Tyr Ser Gly Ser Thr Asn Tyr Asn Pro Ser Leu Lys Arg Val
    50                  55                  60

Thr Ile Ser Val Asp Thr Ser Lys Asn Gln Phe Ser Leu Lys Leu Ser
65                  70                  75                  80

Ser Val Thr Ala Ala Asp Ala Val Tyr Tyr Cys Ala Arg His Gly Leu
                85                  90                  95

Gly Trp Asp Leu Tyr Tyr Phe Asp Tyr Trp Gly Gln Gly Thr Leu Val
            100                 105                 110

Pro Val Ser Ser
            115

<210> SEQ ID NO 82
<211> LENGTH: 108
<212> TYPE: PRT
<213> ORGANISM: Artificial sequence
<220> FEATURE:
<223> OTHER INFORMATION: Synthetic peptide

<400> SEQUENCE: 82

Gln Ser Val Leu Thr Gln Pro Pro Ser Val Ser Gly Ala Thr Gly Gln
1               5                   10                  15

Arg Val Thr Ile Ser Cys Thr Gly Ser Ser Ser Asn Ile Gly Ala Gly
            20                  25                  30

Tyr Asp Val His Trp Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Asp Ser Ser Leu Ser
                85                  90                  95

Gly Tyr Val Phe Gly Thr Gly Thr Lys Val Thr Val
            100                 105

```
<210> SEQ ID NO 83
<211> LENGTH: 118
<212> TYPE: PRT
<213> ORGANISM: Artificial sequence
<220> FEATURE:
<223> OTHER INFORMATION: Synthetic peptide

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Ala Ala Tyr
65                  70                  75                  80

Met Glu Leu Ser Ser Leu Ile Ser Glu Asp Thr Ala Val Tyr Tyr Cys
                85                  90                  95

Ala Ser Val Thr Ser Arg Tyr Trp Gly Gln Gly Thr Leu Val Thr Val
            100                 105                 110

Ser Ser Ala Ser Thr Lys
        115

<210> SEQ ID NO 84
<211> LENGTH: 109
<212> TYPE: PRT
<213> ORGANISM: Artificial sequence
<220> FEATURE:
<223> OTHER INFORMATION: Synthetic peptide

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln His Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Cys Gln Gln His Gly Ile Ser Pro Pro
                85                  90                  95

Phe Met Tyr Thr Phe Gly Gln Gly Thr Lys Leu Glu Ile
            100                 105

<210> SEQ ID NO 85
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 85

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30
```

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Asp Leu Gly Ile Ala Ala Ala Gly Tyr Phe Asp
                100                 105                 110

Tyr Trp Gly Gln Gly Thr Leu Val Thr Val Ser Ser
            115                 120

<210> SEQ ID NO 86
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 86

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Gly Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Pro Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Leu Thr
                 85                  90                  95

Phe Gly Gly Gly Thr Lys Val Glu Ile
                100                 105

<210> SEQ ID NO 87
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 87

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Asp Leu Gly Ile Ala Ala Ala Gly Asp Phe Asp
            100                 105                 110

Tyr Trp Gly Gln Gly Thr Leu Val Thr Val Ser Ser
        115                 120

<210> SEQ ID NO 88
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Gly Ser Asn Trp Pro Thr
                85                  90                  95

Phe Gly Gly Gly Thr Lys Val Glu Ile
            100                 105

<210> SEQ ID NO 89
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 89

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Asp Tyr Ala
    50                  55                  60

Val Ser Val Lys Ser Arg Ile Thr Ile Asn Pro Asp Thr Ser Lys Asn
65                  70                  75                  80

Gln Val Ser Leu Gln Leu Asn Ser Val Thr Pro Glu Asp Thr Ala Val
                85                  90                  95

Tyr Tyr Cys Ala Arg Asp Leu Gly Pro Ala Ala Ala Ala Asp Phe Asp
            100                 105                 110

Tyr Trp Gly Gln Gly Thr Leu Val Thr Val Ser Ser
        115                 120

<210> SEQ ID NO 90
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Ser Asp Ala Ser Asn Arg Ala Thr Gly Ile Pro Ala Arg Phe Ser Gly
50                  55                  60

Ser Gly Ser Gly Thr Asn Phe Thr Leu Thr Ile Ser Ser Leu Glu Pro
65                  70                  75                  80

Glu Asp Phe Ala Val Phe Tyr Cys His Gln His Phe Asn Trp Pro Thr
                85                  90                  95

Phe Gly Gly Gly Thr Lys Val Glu Ile
            100                 105

<210> SEQ ID NO 91
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 91

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Asp Tyr Ala
    50                  55                  60

Val Ser Val Lys Thr Arg Ile Thr Ile Asn Pro Asp Thr Ser Lys Asn
65                  70                  75                  80

Gln Leu Ser Leu His Leu Lys Ser Val Thr Pro Glu Asp Thr Ala Val
                85                  90                  95

Tyr Tyr Cys Ala Arg Asp Leu Gly Val Thr Ala Ala Asp Phe Asp
            100                 105                 110

Phe Trp Gly Gln Gly Thr Leu Val Thr Val Ser Ser
        115                 120

<210> SEQ ID NO 92
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Ser Asp Ala Ser Asn Arg Ala Thr Gly Ile Pro Ala Arg Phe Ser Gly
50                  55                  60

-continued

Ser Gly Ser Gly Thr Asn Phe Thr Leu Thr Ile Ser Ser Leu Glu Pro
 65                  70                  75                  80

Glu Asp Phe Ala Val Phe Tyr Cys His Gln His Phe Asn Trp Pro Thr
                 85                  90                  95

Phe Gly Gly Gly Thr Lys Val Glu Ile
            100                 105

<210> SEQ ID NO 93
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 93

Gln Val Gln Leu Gln Gln Ser Gly Pro Gly Leu Val Lys Pro Ser Gln
1               5                   10                  15

Thr Leu Ser Leu Asn Cys Ala Ile Ser Gly Asp Ser Val Ser Ser Asn
            20                  25                  30

Thr Ala Ala Trp Asn Trp Ile Arg Gln Ser Pro Ser Arg Gly Leu Glu
        35                  40                  45

Trp Leu Gly Arg Thr Tyr Tyr Arg Ser Arg Trp Tyr His Asp Tyr Ala
    50                  55                  60

Leu Ser Val Lys Ser Arg Ile Ser Ile Asn Pro Asp Thr Ser Lys Asn
65                  70                  75                  80

Gln Phe Ser Leu Gln Leu Asn Ser Val Ser Pro Glu Asp Thr Ala Ile
                85                  90                  95

Tyr Tyr Cys Ala Arg Asp Leu Gly Leu Ala Ala Ala Asp Phe Asp
            100                 105                 110

Phe Trp Gly Gln Gly Thr Leu Val Ile Val Ser Ser
        115                 120

<210> SEQ ID NO 94
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 94

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln His Arg Ser Trp Pro Thr
                85                  90                  95

Phe Gly Gly Gly Thr Lys Val Glu Ile
            100                 105

<210> SEQ ID NO 95
<211> LENGTH: 120
<212> TYPE: PRT
<213> ORGANISM: Artificial sequence

```
<220> FEATURE:
<223> OTHER INFORMATION: Synthetic polypeptide

<400> SEQUENCE: 95

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Gly Leu Gly Trp Asp Leu Tyr Tyr Phe Asp Tyr Trp Gly Gln
            100                 105                 110

Gly Thr Leu Val Pro Val Ser Ser
            115                 120

<210> SEQ ID NO 96
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 96

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu
            100                 105                 110

<210> SEQ ID NO 97
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 97

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asn Tyr
            20                  25                  30

Tyr Trp Ser Trp Ile Arg Gln Pro Pro Gly Lys Gly Leu Glu Trp Ile
        35                  40                  45
```

Gly Tyr Ile Tyr Tyr Ser Gly Asn Thr Glu Asn Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg His Gly Leu Gly Trp Asp Leu Tyr Tyr Phe Asp Tyr Trp Gly Gln
             100                 105                 110

Gly Thr Leu Val Pro Val Ser Ser
            115                 120

<210> SEQ ID NO 98
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 98

Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Thr Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ile Gly Tyr Val Phe Gly Thr Gly Thr Lys Val Ser Val Leu
            100                 105                 110

<210> SEQ ID NO 99
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 99

Gln Val Gln Leu Gln Gln Ser Gly Pro Gly Leu Val Lys Pro Ser Glu
  1               5                  10                  15

Thr Leu Ser Leu Thr Cys Thr Val Ser Gly Gly Ser Ile Ser Asn Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Asn Gly Asn Thr Asp Tyr Asn Ser Ser Leu Lys
     50                  55                  60

Ser Arg Val Thr Met Ser Val Asp Ser Ser Lys Asn Gln Phe Ser Leu
 65                  70                  75                  80

Thr Leu Lys Ser Met Thr Ala Ala Asp Thr Ala Val Tyr Tyr Cys Ala
                 85                  90                  95

Arg His Gly Ser Gly Trp Asp Leu Tyr Tyr Phe Asp Tyr Trp Gly Gln
            100                 105                 110

Gly Ile Leu Val Thr Ala Ser Ser
            115                 120

```
<210> SEQ ID NO 100
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 100

Gln Ser Val Leu Thr Gln Pro Pro Ser Val Ser Gly Ala Pro Gly Gln
1               5                   10                  15

Arg Val Thr Ile Ser Cys Thr Gly Thr Ser Leu Asn Ile Gly Ala Gly
            20                  25                  30

Tyr Asp Val Gln Trp Tyr Gln Gln Leu Pro Gly Thr Ala Pro Lys Leu
        35                  40                  45

Leu Ile Tyr Ser Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ala Ser
                85                  90                  95

Leu Lys Gly Tyr Val Phe Gly Pro Gly Thr Lys Val Thr Val Leu
            100                 105                 110

<210> SEQ ID NO 101
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Ala Ala Tyr
65                  70                  75                  80

Met Glu Leu Ser Ser Leu Ile Ser Glu Asp Thr Ala Val Tyr Tyr Cys
                85                  90                  95

Ala Ser Val Thr Ser Arg Tyr Trp Gly Gln Gly Thr Leu Val Thr Val
            100                 105                 110

Ser Ser

<210> SEQ ID NO 102
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Ser Leu Ala Trp Tyr Gln His Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln His Gly Ile Ser Pro
                 85                  90                  95

Pro Phe Met Tyr Thr Phe Gly Gln Gly Thr Arg Leu Glu Ile
            100                 105                 110

<210> SEQ ID NO 103
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 103

Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
            35                  40                  45

Gly Gly Ile Ile Pro Ile Leu Gly Val Thr Asn Tyr Ala Gln Lys Phe
 50                      55                  60

Gln Gly Arg Val Thr Ile Thr Ala Asp Lys Ser Thr Ser Thr Val Tyr
 65                  70                  75                  80

Ile Glu Leu Ser Ser Leu Arg Ser Glu Asp Thr Ala Val Tyr Tyr Cys
                 85                  90                  95

Ala Ser Val Thr Ser Gly Tyr Trp Gly Gln Gly Thr Leu Val Thr Val
            100                 105                 110

Ser Ser

<210> SEQ ID NO 104
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 104

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Ser Ser Ser
             20                  25                  30

Tyr Leu Ala Trp Tyr Gln Gln Lys Pro Gly Gln Ala Pro Arg Leu Leu
            35                  40                  45

Ile Lys Ser Ala Ser Ser Arg Ala Ile Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln His Tyr Gly Ser Ser Pro
                 85                  90                  95

Ala Phe Met Tyr Thr Phe Gly Gln Gly Thr Lys Leu Glu Ile
            100                 105                 110
```

```
<210> SEQ ID NO 105
<211> LENGTH: 15
<212> TYPE: PRT
<213> ORGANISM: Artificial Sequence
<220> FEATURE:
<223> OTHER INFORMATION: Synthetic peptide

<400> SEQUENCE: 105

Gly Ser Gly Ser Gly Ser Gly Met Gln Ala Glu Gly Arg Gly Thr
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic peptide

<400> SEQUENCE: 106

Ser Gly Met Gln Ala Glu Gly Arg Gly Thr Gly Gly Ser Thr Gly
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic peptide

<400> SEQUENCE: 107

Glu Gly Arg Gly Thr Gly Gly Ser Thr Gly Asp Ala Asp Gly Pro
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic peptide

<400> SEQUENCE: 108

Gly Gly Ser Thr Gly Asp Ala Asp Gly Pro Gly Gly Pro Gly Ile
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic peptide

<400> SEQUENCE: 109

Asp Ala Asp Gly Pro Gly Gly Pro Gly Ile Pro Asp Gly Pro Gly
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic peptide

<400> SEQUENCE: 110

Gly Gly Pro Gly Ile Pro Asp Gly Pro Gly Gly Asn Ala Gly Gly
1               5                   10                  15
```

<210> SEQ ID NO 111
<211> LENGTH: 15
<212> TYPE: PRT
<213> ORGANISM: Artificial Sequence
<220> FEATURE:
<223> OTHER INFORMATION: Synthetic peptide

<400> SEQUENCE: 111

Pro Asp Gly Pro Gly Gly Asn Ala Gly Gly Pro Gly Glu Ala Gly
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide

<400> SEQUENCE: 112

Gly Asn Ala Gly Gly Pro Gly Glu Ala Gly Ala Thr Gly Gly Arg
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic peptide

<400> SEQUENCE: 113

Pro Gly Glu Ala Gly Ala Thr Gly Gly Arg Gly Pro Arg Gly Ala
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic peptide

<400> SEQUENCE: 114

Ala Thr Gly Gly Arg Gly Pro Arg Gly Ala Gly Ala Ala Arg Ala
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic peptide

<400> SEQUENCE: 115

Gly Pro Arg Gly Ala Gly Ala Ala Arg Ala Ser Gly Pro Gly Gly
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic peptide

<400> SEQUENCE: 116

Gly Ala Ala Arg Ala Ser Gly Pro Gly Gly Gly Ala Pro Arg Gly
1               5                   10                  15

```
<210> SEQ ID NO 117
<211> LENGTH: 15
<212> TYPE: PRT
<213> ORGANISM: Artificial Sequence
<220> FEATURE:
<223> OTHER INFORMATION: Synthetic peptide

<400> SEQUENCE: 117

Ser Gly Pro Gly Gly Gly Ala Pro Arg Gly Pro His Gly Gly Ala
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic peptide

<400> SEQUENCE: 118

Gly Ala Pro Arg Gly Pro His Gly Gly Ala Ala Ser Gly Leu Asn
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthetic peptide

<400> SEQUENCE: 119

Pro His Gly Gly Ala Ala Ser Gly Leu Asn Gly Cys Cys Arg Cys
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic peptide

<400> SEQUENCE: 120

Ala Ser Gly Leu Asn Gly Cys Cys Arg Cys Gly Ala Arg Gly Pro
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Synthetic peptide

<400> SEQUENCE: 121

Gly Cys Cys Arg Cys Gly Ala Arg Gly Pro Glu Ser Arg Leu Leu
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Synthetic peptide

<400> SEQUENCE: 122

Gly Ala Arg Gly Pro Glu Ser Arg Leu Leu Glu Phe Tyr Leu Ala
1               5                   10                  15
```

```
<210> SEQ ID NO 123
<211> LENGTH: 15
<212> TYPE: PRT
<213> ORGANISM: Artificial Sequence
<220> FEATURE:
<223> OTHER INFORMATION: Synthetic peptide

<400> SEQUENCE: 123

Glu Ser Arg Leu Leu Glu Phe Tyr Leu Ala Met Pro Phe Ala Thr
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Synthetic peptide

<400> SEQUENCE: 124

Glu Phe Tyr Leu Ala Met Pro Phe Ala Thr Pro Met Glu Ala Glu
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Synthetic peptide

<400> SEQUENCE: 125

Met Pro Phe Ala Thr Pro Met Glu Ala Glu Leu Ala Arg Arg Ser
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthetic peptide

<400> SEQUENCE: 126

Pro Met Glu Ala Glu Leu Ala Arg Arg Ser Leu Ala Gln Asp Ala
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthetic peptide

<400> SEQUENCE: 127

Leu Ala Arg Arg Ser Leu Ala Gln Asp Ala Pro Pro Leu Pro Val
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic peptide

<400> SEQUENCE: 128

Leu Ala Gln Asp Ala Pro Pro Leu Pro Val Pro Gly Val Leu Leu
1               5                   10                  15
```

```
<210> SEQ ID NO 129
<211> LENGTH: 15
<212> TYPE: PRT
<213> ORGANISM: Artificial Sequence
<220> FEATURE:
<223> OTHER INFORMATION: Synthetic peptide

<400> SEQUENCE: 129

Pro Pro Leu Pro Val Pro Gly Val Leu Leu Lys Glu Phe Thr Val
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthetic peptide

<400> SEQUENCE: 130

Pro Gly Val Leu Leu Lys Glu Phe Thr Val Ser Gly Asn Ile Leu
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic peptide

<400> SEQUENCE: 131

Lys Glu Phe Thr Val Ser Gly Asn Ile Leu Thr Ile Arg Leu Thr
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic peptide

<400> SEQUENCE: 132

Ser Gly Asn Ile Leu Thr Ile Arg Leu Thr Ala Ala Asp His Arg
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic peptide

<400> SEQUENCE: 133

Thr Ile Arg Leu Thr Ala Ala Asp His Arg Gln Leu Gln Leu Ser
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthetic peptide

<400> SEQUENCE: 134

Ala Ala Asp His Arg Gln Leu Gln Leu Ser Ile Ser Ser Cys Leu
1               5                   10                  15
```

```
<210> SEQ ID NO 135
<211> LENGTH: 15
<212> TYPE: PRT
<213> ORGANISM: Artificial Sequence
<220> FEATURE:
<223> OTHER INFORMATION: Synthetic peptide

<400> SEQUENCE: 135

Gln Leu Gln Leu Ser Ile Ser Ser Cys Leu Gln Gln Leu Ser Leu
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic peptide

<400> SEQUENCE: 136

Ile Ser Ser Cys Leu Gln Gln Leu Ser Leu Leu Met Trp Ile Thr
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Synthetic peptide

<400> SEQUENCE: 137

Gln Gln Leu Ser Leu Leu Met Trp Ile Thr Gln Cys Phe Leu Pro
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic peptide

<400> SEQUENCE: 138

Leu Met Trp Ile Thr Gln Cys Phe Leu Pro Val Phe Leu Ala Gln
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic peptide

<400> SEQUENCE: 139

Gln Cys Phe Leu Pro Val Phe Leu Ala Gln Pro Pro Ser Gly Gln
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic peptide

<400> SEQUENCE: 140

Val Phe Leu Ala Gln Pro Pro Ser Gly Gln Arg Arg Gly Ser Gly
1               5                   10                  15
```

TUMOR SPECIFIC ANTIBODIES AND T-CELL RECEPTORS AND METHODS OF IDENTIFYING THE SAME

This application is a national phase application under 35 U.S.C. § 371 of International Application No. PCT/US2018/057961, filed Oct. 29, 2018, which claims the benefit of U.S. Provisional Patent Application No. 62/578,230, filed Oct. 27, 2017, the entirety of each of which is incorporated herein by reference.

This invention was made with government support under Grant no. R21 AI119368 awarded by the National Institutes of Health and Grant no HDTRA1-12-C-0105 awarded by the Defense Threat Reduction Agency. The government has certain rights in the invention.

This application contains a Sequence Listing, which has been submitted electronically and is hereby incorporated by reference in its entirety. Said Sequence Listing, created on May 10, 2023, is named UTSBP1177US_ST25.txt and is 53,479 bytes in size.

BACKGROUND OF THE INVENTION

1. Field of the Invention

The present invention relates generally to the field of molecular biology and immunology. More particularly, it concerns novel compositions and methods for high throughput discovery and characterization of antitumor antibodies.

2. Description of Related Art

The research and development of cancer therapeutic antibodies, such as Herceptin (Trastuzumab, anti-Her2), Rituxan (Rituximab, anti-CD20), Eribitux/Vectibix (Cetuximab/Panitumumab, anti-EGFR), Avastin (anti-VEGF), and others, has saved many tens of thousands of lives worldwide. Likewise, recently targeted T-cell therapies have received much attention as highly effective for targeting infected and cancerous cells. Both of these therapies offer the potential for: (i) better understood mechanisms of action; (ii) higher specificity and fewer-off target effects; (iii) predictable safety and toxicological profiles. Currently, there are more than 200 antibody therapeutics in clinical trials in the U.S., many of them for cancer treatment and the first T-cell based therapy has recently been approved.

There is a pressing need to identify biologically relevant antibodies and T-cell receptors that exhibit a beneficial effect in controlling diseases. Mammals mount antibody (humoral) immune responses as well T-cell responses against infectious agents, toxins, or cancer cells. Diseased individuals produce circulating antibodies that recognize the disease agent, and in many cases (e.g., in patients that recover from an infection or in cancer patients in remission) these antibodies play a key role in recovery and therapy. Likewise, these subject can produce robust T-cell responses that produce cell expressing T-cell receptors that can specifically recognize infected or cancer cells in the subject. Currently there are no highly effective methods available to identify the circulating antibodies or T-cell receptors in blood and to produce these molecules that are specific to the disease agent and have a therapeutic effect. Therefore, there remains a need to develop more efficient and accurate methods for identifying and characterizing antigen-specific antibodies or T-cell receptors directly from a patient or animal.

SUMMARY OF THE INVENTION

In a first embodiment a method is provided for identifying a cancer-specific antibody and/or T-cell receptor (TCR) sequences, comprising obtaining the mRNA sequences from individual B-cells and/or individual T-cells obtained from a lymph node of a patient having cancer, wherein the B-cells and/or T-cells were obtained from a tumor draining lymph node and wherein the obtained mRNA sequences comprise sequences encoding paired VH and VL and/or paired T-cell receptor polypeptides; and using the mRNA sequences to identify the amino acid sequences encoding the cancer-specific antibody and/or TCR polypeptides. Further aspects of methods provided herein are detailed in McDaniel et al., 2018, incorporated herein by reference in its entirety.

In a further embodiment a method is provided for identifying a cancer-specific antibody and/or T-cell receptor (TCR) sequences, comprising:
a) obtaining the mRNA sequences from individual B-cells and/or individual T-cells obtained from a lymph node of a patient having cancer, wherein the B-cells and/or T-cells were obtained from a tumor draining lymph node and wherein the obtained mRNA sequences comprise sequences encoding paired VH and VL and/or paired T-cell receptor polypeptides;
b) obtaining data showing the actual antibody polypeptides and/or T-cells present in the patient; and
c) using the mRNA sequences and the data to identify the amino acid sequences encoding the cancer-specific antibody and/or TCR polypeptides.

In still a further embodiment a method is provided for identifying a cancer-specific antibody and/or T-cell receptor (TCR) sequences, comprising:
a) obtaining the mRNA sequences from individual T-cells obtained from a lymph node of a patient having cancer, wherein the T-cells were obtained from a tumor draining lymph node and wherein the obtained mRNA sequences comprise sequences encoding paired T-cell receptor polypeptides; and
b) obtaining data showing the actual T-cells present in the patient; and
c) using the mRNA sequences and the data to identify the amino acid sequences encoding the cancer-specific TCR polypeptides. In some aspects, obtaining data showing the actual T-cells present in the patient comprises data showing T-cells in circulation. In further aspects, obtaining data showing the actual T-cells present in the patient comprises quantifying tumor reactive T-cells in the patient. For example, quantifying tumor reactive T-cells in the patient can comprise FACS analysis of the T-cells. In yet further aspects, a method of the embodiments comprises producing a mosaic plot of the quantified tumor reactive T-cells in the patient In some embodiments, the present disclosure provides a method for identifying a cancer-specific antibody sequences, comprising:
a) obtaining the mRNA sequences from individual B-cells obtained from a lymph node of a patient having cancer, wherein the B-cells were obtained from a tumor draining lymph node and wherein the obtained mRNA sequences comprise sequences encoding paired VH and VL;
b) obtaining mass spectra data of peptides derived from an antibody from the subject (e.g., peptides derived from antibodies in the serum); and
c) using the mRNA sequences and the mass spectra data to identify the amino acid sequences encoding the cancer-specific antibody.

In some aspects, the method for identifying a cancer-specific antibody and/or T-cell receptor sequences comprises:

a) obtaining the mRNA sequences from individual B-cells obtained from a lymph node of a patient having cancer, wherein the B-cells were obtained from a tumor draining lymph node and wherein the obtained mRNA sequences comprise sequences encoding paired VH and VL polypeptides;

b) obtaining mass spectra data of peptides derived from antibody polypeptides from the subject; and c) using the mRNA sequences and the mass spectra data to identify the amino acid sequences encoding cancer-specific the antibody.

In some aspects, the B cells comprise mature B cells. In one aspect, the mature B cells comprise memory B cells. In another aspect, the mature B cells comprise plasma cells. In some aspects, the cancer-specific antibody is an IgG, IgM, IgE or IgA antibody.

In some aspects, the T-cells are mature T-cells. In some aspects, the T-cells are CD4+ T-cells. In some aspects, the T-cells are CD8+ T-cells. In some aspects, the T-cells are memory T-cells. In some aspects, the T-cells comprise alpha/beta T-cells. In some aspects, the method further comprises identifying the amino acid sequences encoding the cancer-specific paired alpha and beta TCR polypeptides. In some aspects, the T-cells comprise gamma/delta T-cells. In some aspects a method further comprises identifying the amino acid sequences encoding the cancer-specific paired gamma and delta TCR polypeptides.

In some aspects, the tumor draining lymph node of the embodiments is the subsegmental, segmental, lobar, interlobar, hilar, mediastinal, supratrochlear, deltoideopectoral, lateral, pectoral, subscapular, intermediate, subclavicular, superficial inguinal, deep inguinal, popliteal, facial buccinators, facial nasolabial, prostate, mandibular, submental, occipital, mastoid/retroauricular, parotid, deep preauricular, deep infra-auricular, deep intraglandular, deep cervical, deep anterior cervical, pretracheal, paratracheal, prelaryngeal, thyroid, deep lateral cervical, superior deep cervical, inferior deep cervical, retropharyngeal, jugulodigastric, anterior cervical, lateral cervical, supraclavicular, retroaortic, lateral aortic, celiac, gastric, hepatic, splenic, superior mesenteric, mesenteric, ileocolic, mesocolic, inferior mesenteric, or pararectal lymph node. In some aspects, the tumor draining lymph node is a primary tumor draining lymph node. In some aspects, the tumor draining lymph node is a lymph node that drains a tumor metastasis. In some aspects, the tumor is a solid tumor.

In some aspects, step a) of the method for identifying a cancer-specific antibody and/or T-cell receptor sequences comprises determining the mRNA sequences from individual B-cells and/or individual T-cells encoding paired VH and VL and/or paired T-cell receptor polypeptides. In another aspect, the method further comprises using the mRNA sequences to quantify the number of individual B-cells and/or individual T-cells encoding each unique antibody and/or TCR polypeptide.

In some aspects, the method further comprises producing the identified cancer-specific antibody and/or TCR polypeptide. In some aspects, the method further comprises producing a chimeric antigen receptor based on the identified cancer-specific antibody and/or TCR polypeptide. In some aspects the method further comprises identifying the binding target for the cancer-specific antibody and/or TCR polypeptide. In another aspect, the method further comprises measuring the affinity of the cancer-specific antibody and/or TCR polypeptide for its binding target.

In some aspects, the method further comprises identifying the amino acid sequences encoding a plurality of cancer-specific antibody and/or TCR polypeptides.

In some aspects, the method further comprises selecting one or more unique antibody and/or TCR polypeptides based on the number of individual B-cells and/or T-cells producing the polypeptides and producing the selected cancer-specific antibody and/or TCR polypeptide.

In some aspects, the mRNA sequences from individual B-cells and/or individual T-cells are determined by high-throughput DNA sequencing. In further aspects, the high-throughput sequencing comprises sequencing-by-synthesis, sequencing-by-ligation, sequencing-by-hybridization, single molecule DNA sequencing, multiplex polony sequencing, nanopore sequencing, or a combination thereof.

In some aspects, obtaining the mRNA sequences involves the use of a thermostable reverse transcriptase. In some aspects, the thermostable reverse transcriptase has proofreading activity.

In some aspects, obtaining mass spectra data of peptides derived from an antibody from the subject comprises the use of high-performance liquid chromatography (HPLC). In some aspects, the mass spectra data is from peptides obtained from the serum of the patient. In other aspects, the mass spectra data is from peptides obtained from the tumor draining lymph node of the patient. In other aspects, the mass spectra data is from peptides obtained from the tumor of the patient.

In some aspects, obtaining mass spectra data of peptides derived from an antibody from the subject further comprises isolating or enriching a selected class of antibodies and/or TCR polypeptides.

In some aspects, obtaining mass spectra data of peptides derived from an antibody from the subject further comprises isolating or enriching serum antibodies that bind to a predetermined antigen. In some aspects, obtaining mass spectra data of peptides derived from an antibody from the subject further comprises isolating or enriching CDR3-containing fragments of serum antibodies. In some aspects, obtaining mass spectra data of peptides derived from an antibody from the subject further comprises preparing CDR3-containing peptide fragments from serum antibodies using a protease that is identified based on the sequence information.

In some aspects, the method for identifying a cancer-specific antibody and/or T-cell receptor (TCR) sequences, further comprises reporting the identified sequence.

In some aspects, obtaining mass spectra data of peptides derived from an antibody from the subject further comprises determining the abundancy level of the antibody and/or TCR polypeptides. In some aspects, the method further comprising identifying the antibody and/or TCR polypeptides that exhibit at least a threshold level of abundancy. In further aspects, the method comprises producing identified antibody and/or TCR polypeptides that exhibit at least a threshold level of abundancy.

In a further embodiment there is provided a mosaic plot of data showing quantified information of tumor specific B-cell and/or T-cells produced by a method of the embodiments. In some aspects a mosaic plot comprises data showing quantified individual tumor specific B-cells and/or individual tumor specific T-cells encoding each unique antibody and/or TCR polypeptide. In a further aspect, there is provided a computer readable media comprising a mosaic plot of the embodiments.

In a further embodiment the present disclosure provides an isolated monoclonal antibody, wherein the antibody specifically binds to NY-ESO-1 and comprises:

(I)
- (a) a first VH CDR at least about 80% identical (e.g., at least 85%, 90% or 95% identical) to VH CDR1 of BC2-3G1 (GDSVSSNSAA; SEQ ID NO: 1), BC2-3G2 (GDSVSSNSAA; SEQ ID NO: 1), BC2-3G3 (GDSVSSNSAA; SEQ ID NO: 1), BC2-3G4 (GDSVSSNTAA; SEQ ID NO: 2), or BC2-3G0 (GDSVSSNSAA; SEQ ID NO: 1);
- (b) a second VH CDR at least about 80% identical (e.g., at least 85%, 90% or 95% identical) to VH CDR2 of BC2-3G1 (TYYRSKWYN; SEQ ID NO: 3), BC2-3G2 (TYYRSKWYS; SEQ ID NO: 4), BC2-3G3 (TYYRSKWYS; SEQ ID NO: 4), BC2-3G4 (TYYRSRWYH; SEQ ID NO: 5), or BC2-3G0 (TYYRSKWYN; SEQ ID NO: 3);
- (c) a third VH CDR at least about 80% identical (e.g., at least 85%, 90% or 95% identical) to VH CDR3 of BC2-3G1 (CARDLGIAAAGDFDYW; SEQ ID NO: 6), BC2-3G2 (CARDLGPAAAADFDYW; SEQ ID NO: 7), BC2-3G3 (CARDLGVTAAADFDFW; SEQ ID NO: 8), BC2-3G4 (CARDLGLAAAADFDFW; SEQ ID NO: 9), or BC2-3G0 (CARDLGIAAAGYFDYW; SEQ ID NO: 16);
- (d) a first VL CDR at least about 80% identical (e.g., at least 85%, 90% or 95% identical) to VL CDR1 of BC2-3G1 (QGVSSY; SEQ ID NO: 10), BC2-3G2 (QSVSSY; SEQ ID NO: 11), BC2-3G3 (QSVSSY; SEQ ID NO: 11), BC2-3G4 (QSVSSY; SEQ ID NO: 11), or BC2-3G0 (QGVSSY; SEQ ID NO: 10);
- (e) a second VL CDR at least about 80% identical (e.g., at least 85%, 90% or 95% identical) to VL CDR2 of BC2-3G1 (DAS; SEQ ID NO: 12), BC2-3G2 (DAS; SEQ ID NO: 12), BC2-3G3 (DAS; SEQ ID NO: 12), BC2-3G4 (DAS; SEQ ID NO: 12), or BC2-3G0 (DAS; SEQ ID NO: 12); and
- (f) a third VL CDR at least about 80% identical (e.g., at least 85%, 90% or 95% identical) to VL CDR3 of BC2-3G1 (CHQGSNWPTF; SEQ ID NO: 13), BC2-3G2 (CHQHFNWPTF; SEQ ID NO: 14), BC2-3G3 (CHQHFNWPTF; SEQ ID NO: 14), BC2-3G4 (CHQHRSWPTF; SEQ ID NO: 15) or BC2-3G0 (CQQRSNWLTF; SEQ ID NO: 17); or (II)
- (a) a first VH CDR at least about 80% identical (e.g., at least 85%, 90% or 95% identical) to VH CDR1 of BC2-4G0 (GGSISSY; SEQ ID NO: 18), BC2-4G1 (GGSITNY; SEQ ID NO: 19), or BC2-4G2 (GGSISNY; SEQ ID NO: 20);
- (b) a second VH CDR at least about 80% identical (e.g., at least 85%, 90% or 95% identical) to VH CDR2 of BC2-4G0 (IYYSGST; SEQ ID NO: 21), BC2-4G1 (IYYSGNT; SEQ ID NO: 22), or BC2-4G2 (IYYNGNT; SEQ ID NO: 23);
- (c) a third VH CDR at least about 80% identical (e.g., at least 85%, 90% or 95% identical) to VH CDR3 of BC2-4G0 (CARHGLGWDLYYFDYW; SEQ ID NO: 24), BC2-4G1 (CARHGLGWDLYYFDYW; SEQ ID NO: 24), or BC2-4G2 (CARHGSGWDLYYFDYW; SEQ ID NO: 25);
- (d) a first VL CDR at least about 80% identical (e.g., at least 85%, 90% or 95% identical) to VL CDR1 of BC2-4G0 (SSNIGAGYD; SEQ ID NO: 26), BC2-4G1 (SSNIGAGYD; SEQ ID NO: 26), or BC2-4G2 (SLNIGAGYD; SEQ ID NO: 27);
- (e) a second VL CDR at least about 80% identical (e.g., at least 85%, 90% or 95% identical) to VL CDR2 of BC2-4G0 (GNS; SEQ ID NO: 28), BC2-4G1 (GNT; SEQ ID NO: 29), or BC2-4G2 (SNN; SEQ ID NO: 30); and
- (f) a third VL CDR at least about 80% identical (e.g., at least 85%, 90% or 95% identical) to VL CDR3 of BC2-4G0 (CQSYDSSLSGYVF; SEQ ID NO: 31), BC2-4G1 (CQSYDSSLIGYVF; SEQ ID NO: 32), or BC2-4G2 (CQSYDASLKGYVF; SEQ ID NO: 33); or (III)
- (a) a first VH CDR at least about 80% identical (e.g., at least 85%, 90% or 95% identical) to VH CDR1 of BC2-5G1 (GGTFSSYA; SEQ ID NO: 34), or BC2-5G2 (GGTFSSYA; SEQ ID NO: 34);
- (b) a second VH CDR at least about 80% identical (e.g., at least 85%, 90% or 95% identical) to VH CDR2 of BC2-5G1 (IIPILGIA; SEQ ID NO: 35), or BC2-5G2 (IIPILGVT; SEQ ID NO: 36);
- (c) a third VH CDR at least about 80% identical (e.g., at least 85%, 90% or 95% identical) to VH CDR3 of BC2-5G1 (CASVTSRYW; SEQ ID NO: 44), or BC2-5G2 (CASVTSGYW; SEQ ID NO: 37);
- (d) a first VL CDR at least about 80% identical (e.g., at least 85%, 90% or 95% identical) to VL CDR1 of BC2-5G1 (QSVSSSS; SEQ ID NO: 38), or BC2-5G2 (QSISSSY; SEQ ID NO: 39);
- (e) a second VL CDR at least about 80% identical (e.g., at least 85%, 90% or 95% identical) to VL CDR2 of BC2-5G1 (GAS; SEQ ID NO: 40), or BC2-5G2 (SAS; SEQ ID NO: 41); and
- (f) a third VL CDR at least about 80% identical (e.g., at least 85%, 90% or 95% identical) to VL CDR3 of BC2-5G1 (CQQHGISPPFMYTF; SEQ ID NO: 42), or BC2-5G2 (CQHYGSSPAFMYTF; SEQ ID NO: 43).

In yet further embodiments the present disclosure provides an isolated monoclonal antibody, wherein the antibody specifically binds to NY-ESO-1 and comprises:

(I)
- (a) a first VH CDR identical, or has 1, 2 or 3 amino acid substitutions relative, to VH CDR1 of BC2-3G1 (GDSVSSNSAA; SEQ ID NO: 1), BC2-3G2 (GDSVSSNSAA; SEQ ID NO: 1), BC2-3G3 (GDSVSSNSAA; SEQ ID NO: 1), BC2-3G4 (GDSVSSNTAA; SEQ ID NO: 2), or BC2-3G0 (GDSVSSNSAA; SEQ ID NO: 1);
- (b) a second VH CDR identical, or has 1, 2 or 3 amino acid substitutions relative, to VH CDR2 of BC2-3G1 (TYYRSKWYN; SEQ ID NO: 3), BC2-3G2 (TYYRSKWYS; SEQ ID NO: 4), BC2-3G3 (TYYRSKWYS; SEQ ID NO: 4), BC2-3G4 (TYYRSRWYH; SEQ ID NO: 5), or BC2-3G0 (TYYRSKWYN; SEQ ID NO: 3);
- (c) a third VH CDR identical, or has 1, 2 or 3 amino acid substitutions relative, to VH CDR3 of BC2-3G1 (CARDLGIAAAGDFDYW; SEQ ID NO: 6), BC2-3G2 (CARDLGPAAAADFDYW; SEQ ID NO: 7), BC2-3G3 (CARDLGVTAAADFDFW; SEQ ID NO: 8), BC2-3G4 (CARDLGLAAAADFDFW; SEQ ID NO: 9), or BC2-3G0 (CARDLGIAAAGYFDYW; SEQ ID NO: 16);
- (d) a first VL CDR identical, or has 1, 2 or 3 amino acid substitutions relative, to VL CDR1 of BC2-3G1 (QGVSSY; SEQ ID NO: 10), BC2-3G2 (QSVSSY; SEQ ID NO: 11), BC2-3G3 (QSVSSY; SEQ ID NO: 11), BC2-3G4 (QSVSSY; SEQ ID NO: 11), or BC2-3G0 (QGVSSY; SEQ ID NO: 10);

(e) a second VL CDR identical, or has 1 amino acid substitution relative, to VL CDR2 of BC2-3G1 (DAS; SEQ ID NO: 12), BC2-3G2 (DAS; SEQ ID NO: 12), BC2-3G3 (DAS; SEQ ID NO: 12), BC2-3G4 (DAS; SEQ ID NO: 12), or BC2-3G0 (DAS; SEQ ID NO: 12); and (f) a third VL CDR identical, or has 1, 2 or 3 amino acid substitutions relative, to VL CDR3 of BC2-3G1 (CHQGSNWPTF; SEQ ID NO: 13), BC2-3G2 (CHQHFNWPTF; SEQ ID NO: 14), BC2-3G3 (CHQHFNWPTF; SEQ ID NO: 14), BC2-3G4 (CHQHRSWPTF; SEQ ID NO: 15) or BC2-3G0 (CQQRSNWLTF; SEQ ID NO: 17); or (II)
(a) a first VH CDR identical, or has 1, 2 or 3 amino acid substitutions relative, to VH CDR1 of BC2-4G0 (GGSISSY; SEQ ID NO: 18), BC2-4G1 (GGSITNY; SEQ ID NO: 19), or BC2-4G2 (GGSISNY; SEQ ID NO: 20);

(b) a second VH CDR identical, or has 1, 2 or 3 amino acid substitutions relative, to VH CDR2 of BC2-4G0 (IYYSGST; SEQ ID NO: 21), BC2-4G1 (IYYSGNT; SEQ ID NO: 22), or BC2-4G2 (IYYNGNT; SEQ ID NO: 23);

(c) a third VH CDR identical, or has 1, 2 or 3 amino acid substitutions relative, to VH CDR3 of BC2-4G0 (CARHGLGWDLYYFDYW; SEQ ID NO: 24), BC2-4G1 (CARHGLGWDLYYFDYW; SEQ ID NO: 24), or BC2-4G2 (CARHGSGWDLYYFDYW; SEQ ID NO: 25);

(d) a first VL CDR identical, or has 1, 2 or 3 amino acid substitutions relative, to VL CDR1 of BC2-4G0 (SSNIGAGYD; SEQ ID NO: 26), BC2-4G1 (SSNIGAGYD; SEQ ID NO: 26), or BC2-4G2 (SLNIGAGYD; SEQ ID NO: 27);

(e) a second VL CDR identical, or has 1 amino acid substitution relative, to VL CDR2 of BC2-4G0 (GNS; SEQ ID NO: 28), BC2-4G1 (GNT; SEQ ID NO: 29), or BC2-4G2 (SNN; SEQ ID NO: 30); and (f) a third VL CDR identical, or has 1, 2 or 3 amino acid substitutions relative, to VL CDR3 of BC2-4G0 (CQSYDSSLSGYVF; SEQ ID NO: 31), BC2-4G1 (CQSYDSSLIGYVF; SEQ ID NO: 32), or BC2-4G2 (CQSYDASLKGYVF; SEQ ID NO: 33); or (III)
(a) a first VH CDR identical, or has 1, 2 or 3 amino acid substitutions relative, to VH CDR1 of BC2-5G1 (GGTFSSYA; SEQ ID NO: 34), or BC2-5G2 (GGTFSSYA; SEQ ID NO: 34);

(b) a second VH CDR identical, or has 1, 2 or 3 amino acid substitutions relative, to VH CDR2 of BC2-5G1 (IIPILGIA; SEQ ID NO: 35), or BC2-5G2 (IIPILGVT; SEQ ID NO: 36);

(c) a third VH CDR identical, or has 1, 2 or 3 amino acid substitutions relative, to VH CDR3 of BC2-5G1 (CASVTSRYW; SEQ ID NO: 44), or BC2-5G2 (CASVTSGYW; SEQ ID NO: 37);

(d) a first VL CDR identical, or has 1, 2 or 3 amino acid substitutions relative, to VL CDR1 of BC2-5G1 (QSVSSSS; SEQ ID NO: 38), or BC2-5G2 (QSISSSY; SEQ ID NO: 39);

(e) a second VL CDR identical, or has 1 amino acid substitution relative, to VL CDR2 of BC2-5G1 (GAS; SEQ ID NO: 40), or BC2-5G2 (SAS; SEQ ID NO: 41); and (f) a third VL CDR identical, or has 1, 2 or 3 amino acid substitutions relative, to VL CDR3 of BC2-5G1 (CQQHGISPPFMYTF; SEQ ID NO: 42), or BC2-5G2 (CQHYGSSPAFMYTF; SEQ ID NO: 43).

In some embodiments the present disclosure provides an isolated monoclonal antibody, wherein the antibody specifically binds to NY-ESO-1 and comprises:

(I)
(a) a first VH CDR identical to VH CDR1 of BC2-3G1 (GDSVSSNSAA; SEQ ID NO: 1), BC2-3G2 (GDSVSSNSAA; SEQ ID NO: 1), BC2-3G3 (GDSVSSNSAA; SEQ ID NO: 1), BC2-3G4 (GDSVSSNTAA; SEQ ID NO: 2), or BC2-3G0 (GDSVSSNSAA; SEQ ID NO: 1);

(b) a second VH CDR identical to VH CDR2 of BC2-3G1 (TYYRSKWYN; SEQ ID NO: 3), BC2-3G2 (TYYRSKWYS; SEQ ID NO: 4), BC2-3G3 (TYYRSKWYS; SEQ ID NO: 4), BC2-3G4 (TYYRSRWYH; SEQ ID NO: 5), or BC2-3G0 (TYYRSKWYN; SEQ ID NO: 3);

(c) a third VH CDR identical to VH CDR3 of BC2-3G1 (CARDLGIAAAGDFDYW; SEQ ID NO: 6), BC2-3G2 (CARDLGPAAAADFDYW; SEQ ID NO: 7), BC2-3G3 (CARDLGVTAAADFDFW; SEQ ID NO: 8), BC2-3G4 (CARDLGLAAAADFDFW; SEQ ID NO: 9), or BC2-3G0 (CARDLGIAAAGYFDYW; SEQ ID NO: 16);

(d) a first VL CDR identical to VL CDR1 of BC2-3G1 (QGVSSY; SEQ ID NO: 10), BC2-3G2 (QSVSSY; SEQ ID NO: 11), BC2-3G3 (QSVSSY; SEQ ID NO: 11), BC2-3G4 (QSVSSY; SEQ ID NO: 11), or BC2-3G0 (QGVSSY; SEQ ID NO: 10);

(e) a second VL CDR identical to VL CDR2 of BC2-3G1 (DAS; SEQ ID NO: 12), BC2-3G2 (DAS; SEQ ID NO: 12), BC2-3G3 (DAS; SEQ ID NO: 12), BC2-3G4 (DAS; SEQ ID NO: 12), or BC2-3G0 (DAS; SEQ ID NO: 12); and (f) a third VL CDR identical to VL CDR3 of BC2-3G1 (CHQGSNWPTF; SEQ ID NO: 13), BC2-3G2 (CHQHFNWPTF; SEQ ID NO: 14), BC2-3G3 (CHQHFNWPTF; SEQ ID NO: 14), BC2-3G4 (CHQHRSWPTF; SEQ ID NO: 15) or BC2-3G0 (CQQRSNWLTF; SEQ ID NO: 17); or (II)
(a) a first VH CDR identical to VH CDR1 of BC2-4G0 (GGSISSY; SEQ ID NO: 18), BC2-4G1 (GGSITNY; SEQ ID NO: 19), or BC2-4G2 (GGSISNY; SEQ ID NO: 20);

(b) a second VH CDR identical to VH CDR2 of BC2-4G0 (IYYSGST; SEQ ID NO: 21), BC2-4G1 (IYYSGNT; SEQ ID NO: 22), or BC2-4G2 (IYYNGNT; SEQ ID NO: 23);

(c) a third VH CDR identical to VH CDR3 of BC2-4G0 (CARHGLGWDLYYFDYW; SEQ ID NO: 24), BC2-4G1 (CARHGLGWDLYYFDYW; SEQ ID NO: 24), or BC2-4G2 (CARHGSGWDLYYFDYW; SEQ ID NO: 25);

(d) a first VL CDR identical to VL CDR1 of BC2-4G0 (SSNIGAGYD; SEQ ID NO: 26), BC2-4G1 (SSNIGAGYD; SEQ ID NO: 26), or BC2-4G2 (SLNIGAGYD; SEQ ID NO: 27);

(e) a second VL CDR identical to VL CDR2 of BC2-4G0 (GNS; SEQ ID NO: 28), BC2-4G1 (GNT; SEQ ID NO: 29), or BC2-4G2 (SNN; SEQ ID NO: 30); and (f) a third VL CDR identical to VL CDR3 of BC2-4G0 (CQSYDSSLSGYVF; SEQ ID NO: 31), BC2-4G1 (CQSYDSSLIGYVF; SEQ ID NO: 32), or BC2-4G2 (CQSYDASLKGYVF; SEQ ID NO: 33); or (III)
(a) a first VH CDR identical to VH CDR1 of BC2-5G1 (GGTFSSYA; SEQ ID NO: 34), or BC2-5G2 (GGTFSSYA; SEQ ID NO: 34);
(b) a second VH CDR identical to VH CDR2 of BC2-5G1 (IIPILGIA; SEQ ID NO: 35), or BC2-5G2 (IIPILGVT; SEQ ID NO: 36);
(c) a third VH CDR identical to VH CDR3 of BC2-5G1 (CASVTSRYW; SEQ ID NO: 44), or BC2-5G2 (CASVTSGYW; SEQ ID NO: 37);
(d) a first VL CDR identical to VL CDR1 of BC2-5G1 (QSVSSSS; SEQ ID NO: 38), or BC2-5G2 (QSISSSY; SEQ ID NO: 39);
(e) a second VL CDR identical to VL CDR2 of BC2-5G1 (GAS; SEQ ID NO: 40), or BC2-5G2 (SAS; SEQ ID NO: 41); and
(f) a third VL CDR identical to VL CDR3 of BC2-5G1 (CQQHGISPPFMYTF; SEQ ID NO: 42), or BC2-5G2 (CQHYGSSPAFMYTF; SEQ ID NO: 43).

In some aspects, the antibody is an IgG, IgM, IgE, IgA or an antigen binding fragment thereof. In some aspects, the antibody is a Fab', a F(ab')2, a F(ab')3, a monovalent scFv, a bivalent scFv, or a single domain antibody. In some aspects, the antibody is a human, humanized antibody or de-immunized antibody. In some aspects, the antibody is conjugated to an imaging agent, a chemotherapeutic agent, a toxin or a radionuclide.

In some embodiments, the present disclosure provides an isolated monoclonal antibody as described herein, in a pharmaceutically acceptable carrier. In some aspects, the antibody in a pharmaceutically acceptable carrier is an IgG, IgM, IgE, IgA or an antigen binding fragment thereof. In some aspects, the antibody is a Fab', a F(ab')2, a F(ab')3, a monovalent scFv, a bivalent scFv, or a single domain antibody. In some aspects, the antibody in a pharmaceutically acceptable carrier is a human, humanized antibody or de-immunized antibody. In some aspects, the antibody in a pharmaceutically acceptable carrier is conjugated to an imaging agent, a chemotherapeutic agent, a toxin or a radionuclide.

In some embodiments, the present disclosure provides an isolated polynucleotide molecule comprising a nucleic acid sequence encoding an antibody VH or VL as specified herein.

In some aspects, the isolated polynucleotide molecule comprising a nucleic acid sequence encoding an antibody VH or VL codes for an IgG, IgM, IgA antibody or an antigen binding fragment thereof.

In a further embodiment there is provide a chimeric antigen receptor comprising an antibody or antigen binding fragment thereof according to the embodiments that binds to NY-ESO-1.

In some embodiments, the present disclosure provides a host cell comprising one or more polynucleotide molecule(s) encoding an antibody or comprising an antibody as specified herein. In some aspects, the antibody is an IgG, IgM, IgA or an antigen binding fragment thereof. In some aspects, the host cell is a mammalian cell, a yeast cell, a bacterial cell, a ciliate cell or an insect cell.

In some embodiments, the present disclosure provides a method of manufacturing an antibody comprising:
(a) expressing one or more polynucleotide molecule(s) encoding a VL and VH chain of an antibody described herein; and
(a) purifying the antibody from the cell.

In some embodiments, the present disclosure provides a method for treating a subject having a cancer comprising administering to a subject an effective amount of an antibody as described herein. In some aspects, the cancer is an NY-ESO-1 positive cancer. In some aspects, the cancer is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer, skin cancer, or synovial cancer. In some aspects, the antibody is in a pharmaceutically acceptable composition. In some aspects, the antibody is administered systemically. In some aspects, the antibody is administered intravenously, intradermally, intratumorally, intramuscularly, intraperitoneally, subcutaneously, or locally.

In some aspects, the method further comprises administering at least a second anticancer therapy to the subject. In some aspects, the second anticancer therapy is a surgical therapy, chemotherapy, radiation therapy, cryotherapy, hormonal therapy, immunotherapy or cytokine therapy.

In some embodiments, the present disclosure provides a method for detecting a cancer in a subject comprising testing for the presence of NY-ESO-1 in a sample from the subject, wherein the testing comprises contacting the sample with an antibody as disclosed herein. In some aspects, the method is defined as an in vitro method.

In some embodiments, the present disclosure provides a method for generating an isotypic mosaic profile antibodies described herein.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4: Phylogenetic analysis of BC2-5G. (A) Maximum likelihood phylogram of BC2-5G. Sub-lineages are defined by different CDR-H3 amino acid sequences. Black nodes represent CDR-H3 sequences that do not exactly match one of the primary sub-lineage clusters. (B) Table illustrating the pairing specificity of CDR-H3 to CDR-L3 among dominant lineage members. (CASVTSRYW, SEQ ID NO: 44; CASVTSGYW, SEQ ID NO: 37; CQQHGISPPFMYTF, SEQ ID NO: 42; CQHYGSSPAFMYTF, SEQ ID NO: 43) (C-D) Representative VH and VL sequences for each pair denoted by '*' in (A). CDR1, CDR2, and CDR3 regions are underlined. (In C, VH1-69=SEQ ID NO: 83; in D, VK3-20=SEQ ID NO: 84)

FIG. 5: Surface plasmon resonance curves of various members of the 3G and 4G lineages across a range of concentrations. A-E) The indicated lineage of BC2 monoclonal antibody was flowed over immobilized NY-ESO-1 at the indicated concentrations to generate SPR curves. F) $K_D$ values were calculated via SPR for each mAb.

FIG. 6: The PEPperMAP® Epitope Mapping of human IgG1 monoclonal antibody BC2-3G(4) was performed against NY-ESO-1/CTAG1B translated into linear overlapping 15 amino acid peptides with a peptide-peptide overlap of 14 amino acids for high-resolution epitope data. The resulting NY-ESO-1/CTAG1B peptide microarrays were incubated with the human IgG1 monoclonal antibody at concentrations of 1 μg/ml (lower plot) and 10 μg/ml (upper plot) in incubation buffer followed by staining with secondary and control antibodies as well as read-out with a LI-COR Odyssey Imaging System. The peptide sequences along the X-axis, from left to right, are represented by SEQ ID NOs: 105-140.

DESCRIPTION OF ILLUSTRATIVE EMBODIMENTS

I. The Present Embodiments

Figure 1A:
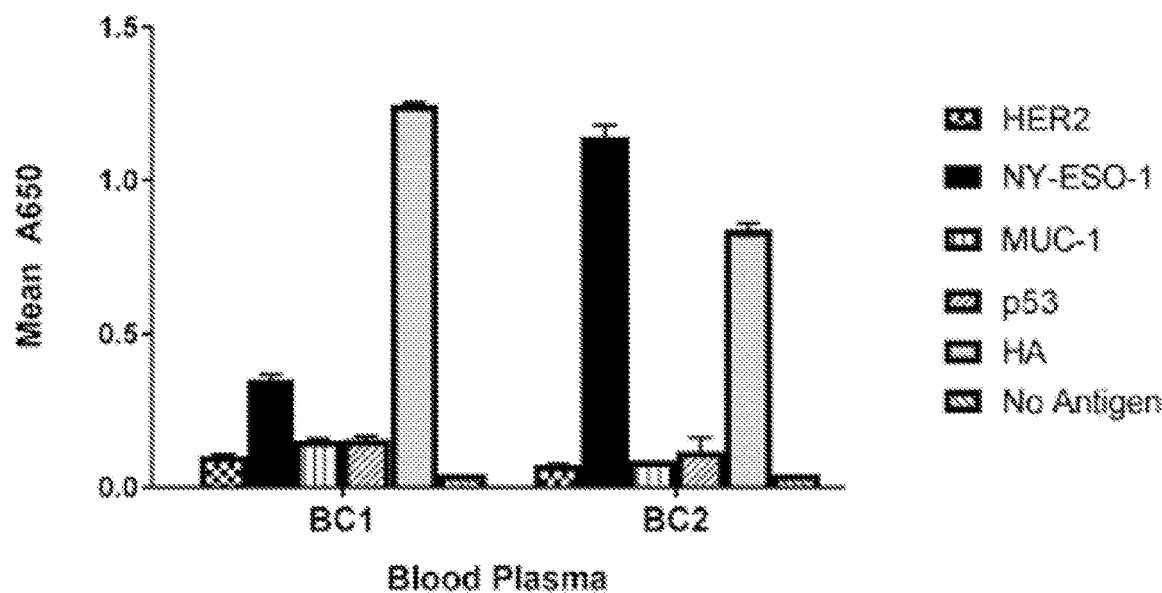
FIG. 1: (A) Plasma ELISA against selected antigens. Blood plasma was screened by ELISA to identify NY-ESO-1 sero-positive patients. The antigen panel included: HER2, NY-ESO-1, MUC-1, p53, and Hemagglutinin Flu b (HA) protein as a positive control. Values represent mean±SD (n=2). BC1 and BC2 were breast cancer samples selected for further study. (B) Mosaic profiles of expanded B cell clones in the SN. NGS reads were down-sampled to normalize the number of reads across patients and isotypes. The size of each square is relative to the frequency of NGS reads assigned to each lineage following down-sampling to normalize the number of reads across patients and isotypes. Expressed antibody lineages are labeled. (C) Selective human antibodies derived from the SN B cells binding to NY-ESO-1. ELISA demonstrating strong positive IgA (BC1-2A) and IgG (BC2-3G and BC2-4G) antibodies binding to NY-ESO-1 from patient BC1 and BC2 and not to HER2 or hemagglutinin Flu B (HA) protein. Values represent mean±SD (n=2).

The present disclosure generally relates to discovering, sequencing, and characterizing antibodies. More particularly the disclosure relates methods for high-throughput sequencing of paired transcripts which are co-expressed in single cells to determine amino acid sequences which comprise immune receptors, and quantitation and characterization of said immune receptors.

The methods of the present disclosure allow for the repertoire of immune receptors and antibodies in an individual organism or population of cells to be determined Particularly, the methods of the present disclosure may aid in determining pairs of polypeptide chains that make up immune receptors. B cells and T cells each express immune receptors; B cells express immunoglobulins, and T cells express T cell receptors (TCRs). Both types of immune receptors consist of two polypeptide chains. Immunoglobulins consist of variable heavy (VH) and variable light (VL) chains. TCRs are of two types: one consisting of an a and a R chain, and one consisting of a γ and a δ chain. Each of the polypeptides in an immune receptor has constant region and a variable region. Variable regions result from recombination and end joint rearrangement of gene fragments on the chromosome of a B or T cell. In B cells additional diversification of variable regions occurs by somatic hypermutation. Thus, the immune system has a large repertoire of receptors, and any given receptor pair expressed by a lymphocyte is encoded by a pair of separate, unique transcripts. Only by knowing the sequence of both transcripts in the pair can one study the receptor as a whole. Knowing the sequences of pairs of immune receptor chains expressed in a single cell is also essential to ascertaining the immune repertoire of a given individual or population of cells.

Currently available methods to analyze multiple transcripts in single cells, such as the two transcripts that comprise adaptive immune receptors, are limited by low throughput and very high instrumentation and reagent costs.

No technology currently exists for rapidly analyzing how many cells express a set of transcripts of interest or, more specifically, for sequencing native lymphocyte receptor chain pairs at very high throughput (greater than 10,000 cells per run). The present disclosure aims to correct these deficiencies by providing a new technique for sequencing multiple transcripts simultaneously at the single-cell level with a throughput two to three orders of magnitude greater than the current state of the art.

One advantage of the methods of the present disclosure is that the methods result in a higher throughput several orders of magnitude larger than the current state of the art. In addition, the present disclosure allows for the ability to link two transcripts for large cell populations in a high throughput manner, faster and at a much lower cost than competing technologies.

II. Antibodies

Certain aspects of the invention provide methods for identifying antibody variable domains or variable domain-coding sequences that are over-represented in serum or B cells. Such skewed representation of antibody variable domains is useful to identify novel antigen binding molecules having high affinity or specificity. Generating antibody or antibody fragments having variable domains with a high level of abundancy allows for the isolation of high affinity binders. The present invention is based, in part, on the discovery that abundancy levels of regions of an antibody variable domain that form the antigen binding pocket, for example CDR3 regions, could correlate with the desired affinity or specificity.

For identifying desired antibody variable domains, certain aspects of the present invention provide methods of determining sequences and distribution of antibody complementarity determining regions (CDRs). Specifically, the sequences of one to six of the complementary determining regions (CDRs) on VH and/or VL could be determined by protein sequencing or nucleic acid sequencing methods. The level of abundancy of variable domains or CDRs could be determined as an absolute level like a concentration or relative level like a rank-order.

Antibodies are globular plasma proteins (~150 kDa) that are also known as immunoglobulins. They have sugar chains added to some of their amino acid residues. In other words, antibodies are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds. Each chain is composed of structural domains called Ig domains. These domains contain about 70-110 amino acids and are classified into different categories (for example, variable or IgV, and constant or IgC) according to their size and function. They have a characteristic immunoglobulin fold in which two beta sheets create a "sandwich" shape, held together by interactions between conserved cysteines and other charged amino acids.

There are five types of human Ig heavy chain denoted by the Greek letters: $\alpha$, $\delta$, $\epsilon$, $\gamma$, and $\mu$. The type of heavy chain present defines the class of antibody; these chains are found in IgA, IgD, IgE, IgG, and IgM antibodies, respectively. Distinct heavy chains differ in size and composition; Ig heavy chains $\alpha$ and $\gamma$ contain approximately 450 amino acids, while $\mu$ and $\epsilon$ have approximately 550 amino acids. Other animals encode analogous immunoglobulin heavy chain classes.

Each heavy chain has two regions, the constant region and the variable region. The constant region is identical in all antibodies of the same isotype, but differs in antibodies of different isotypes. Heavy chains $\gamma$, $\alpha$ and $\delta$ have a constant region composed of three tandem (in a line) Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In humans (and mice) there are two types of Immunoglobulin light chain, which are called lambda ($\lambda$) and kappa ($\kappa$). A light chain has two successive domains: one constant domain and one variable domain. The approximate length of a light chain is 211 to 217 amino acids. Each antibody contains two light chains that are always identical; only one type of light chain, $\kappa$ or $\lambda$, is present per antibody in these species.

The fragment antigen-binding (Fab fragment) is a region on an antibody that binds to antigens. It is composed of one constant and one variable domain of each of the heavy and the light chain. These domains shape the paratope—the antigen-binding site—at the amino terminal end of the monomer.

The two variable domains bind the epitope on their specific antigens. The variable domain is also referred to as the Fv region and is the most important region for binding to antigens. More specifically variable loops, three each on the light ($V_L$) and heavy ($V_H$) chains are responsible for binding to the antigen. These loops are referred to as the Complementarity Determining Regions (CDRs).

A complementarity determining region (CDR) is a short amino acid sequence found in the variable domains of antigen receptor (e.g. immunoglobulin and T cell receptor) proteins that complements an antigen and therefore provides the receptor with its specificity for that particular antigen. CDRs are supported within the variable domains by conserved framework regions (FRs).

Each polypeptide chain of an antigen receptor contains three CDRs (CDR1, CDR2 and CDR3). Since the antigen receptors are typically composed of two polypeptide chains, there are six CDRs for each antigen receptor that can come into contact with the antigen (each heavy and light chain contains three CDRs), twelve CDRs on a single antibody molecule and sixty CDRs on a pentameric IgM molecule. Since most sequence variation associated with immunoglobulins and T cell receptors are found in the CDRs, these regions are sometimes referred to as hypervariable domains. Among these, CDR3 shows the greatest variability as it is encoded by a recombination of the VJ (VDJ in the case of heavy chain) regions.

III. Antibody Variable Region Analysis

In certain aspects of the invention, antibody variable gene (V gene) sequences derived from cDNA may be analyzed. For example, information from such analysis may be used to generate a database of the V genes (V gene database) that give rise to circulating antibodies so that mass spectrometry (MS) spectra of peptides derived from serum antibodies can be assigned and in turn used to identify the respective full length V genes in the database encoding those peptides. In another embodiment, the sequence information may be used to identify abundant variable gene nucleic acids such as mRNA transcripts and generate antibody or antibody fragments based on the abundant variable genes. The abundant variable genes so identified may correspond to antibodies or antibody fragments that have desired specificity or affinity. Methods for analysis of immunoglobulin by sequencing and mass spectrometry are provided, e.g., in U.S. Pat. No. 9,090,674, which is incorporated herein by reference.

From the nucleotide sequences determined by the initial sequencing, putative amino acid sequences for the VH and VL regions can be determined using standard algorithms and software packages (e.g. see the world wide web at mrc-lmb.cam.ac.uk/pubseq/, the Staden package and Gap4 programs). These can be further characterized to determine the CDR (Complementarity Determining Region) parts of the VH and VL sequences, particularly CDR1, CDR2 and CDR3. Methods for determining the putative amino acid sequences and identifying CDR regions are well known in the art. In one particular embodiment, CDR3 sequences are identified by searching for highly conserved sequence motif at the N-terminal region preceding the CDR3. This method could correctly identified >90% of the CDR3 sequences in antibodies. The putative amino acid sequence derived based on the nucleic acid sequencing of B cell cDNA could be used for the shot gun proteomic analysis of serum antibodies in some embodiments.

A variety of methods have been developed for the immortalization or cloning of antibodies from individual B cells. These techniques include hybridoma technology, memory B cell immortalization by viral (EBV) infection, the engineering of memory B cells that express both surface and secreted antibodies, and the cloning of antigen-specific, antibody genes from transient ASC populations, from memory B cells or from splenic plasma cells. Recently microfluidic and nanopatterning devices have been used to increase the throughput of B cells interrogated for antigen binding and for the subsequent cloning of the $V_H$ and $V_L$ genes.

While invaluable for the isolation of monoclonal antibodies, these techniques have several drawbacks: First, most have focused on and, in some cases, are only compatible with certain stages of the B cell life cycle. Thus, extensive studies on terminally differentiated mature plasma ASC have not been done. This leaves unresolved the central issue of whether a particular antibody isolated from B cells is represented at a significant amount in the serum of that individual. Also, there is evidence that plasma cells in the bone marrow are the main compartment for antibody synthesis and are selected on the basis of their affinity and perhaps protective function. Second, single B cell cloning methods are still not efficient enough to provide complete information on the diversity of antibodies in serum, especially with respect to serum concentration and abundancy of specific antibody clones. Third, current attempts to pool recombinant mAbs in order to reconstitute a polyclonal antibody that displays higher therapeutic efficacy cannot possibly capture the true protective effect of sera since the mixing of cloned antibodies is completely ad hoc. The present invention could avoid one or more of these problems by the methods described herein.

In certain embodiments, the mRNA from B cells or directly from one or more lymphoid tissues could be isolated and converted to cDNA. In further embodiments, the cDNA may be subject to $V_H$ and $V_L$ gene isolation. For example, the genes encoding for the variable heavy and the variable light ($V_H$ and $V\kappa,\lambda$) genes could be amplified using specific primers that hybridize to the 5' and 3' ends of the cDNA. Depending on the primers used for cDNA construction, V genes of different Ig classes could be distinguished. For example, the $V_H$ and $V_L$ gene isolation may be based on Ig classes either by using known primer sets of variable gene amplification or, preferably by 3' RACE (rapid amplification of cDNA ends) using a class-specific 3' primer. For example, the class-specific 3' primer may hybridize to the $CH_2$ domain.

IV. Lymphoid Tissues

In certain embodiments, there may be provided methods of identifying antigen-specific variable region sequences by obtaining nucleic acid sequences directly from lymphoid tissues. In optional aspects, B cells may not be separated from the lymphoid tissue where the B cells reside. The method may comprise isolation of primary, secondary, or tertiary lymphoid tissues. Any methods known for isolation of lymphoid tissues may be used.

Lymphoid tissue associated with the lymphatic system is concerned with immune functions in defending the body against the infections and spread of tumors. It consists of connective tissue with various types of white blood cells enmeshed in it, most numerous being the lymphocytes.

The lymphoid tissue may be primary, secondary, or tertiary depending upon the stage of lymphocyte development and maturation it is involved in. (The tertiary lymphoid tissue typically contains far fewer lymphocytes, and assumes an immune role only when challenged with antigens that result in inflammation. It achieves this by importing the lymphocytes from blood and lymph.

The central or primary lymphoid organs generate lymphocytes from immature progenitor cells. The thymus and the bone marrow constitute the primary lymphoid tissues involved in the production and early selection of lymphocytes.

Secondary or peripheral lymphoid organs maintain mature naive lymphocytes and initiate an adaptive immune response. The peripheral lymphoid organs are the sites of lymphocyte activation by antigen. Activation leads to clonal expansion and affinity maturation. Mature Lymphocytes recirculate between the blood and the peripheral lymphoid organs until they encounter their specific antigen.

Secondary lymphoid tissue provides the environment for the foreign or altered native molecules (antigens) to interact with the lymphocytes. It is exemplified by the lymph nodes, and the lymphoid follicles in tonsils, Peyer's patches, spleen, adenoids, skin, etc. that are associated with the mucosa-associated lymphoid tissue (MALT).

A lymph node is an organized collection of lymphoid tissue, through which the lymph passes on its way to returning to the blood. Lymph nodes are located at intervals along the lymphatic system. Several afferent lymph vessels bring in lymph, which percolates through the substance of the lymph node, and is drained out by an efferent lymph vessel.

The substance of a lymph node consists of lymphoid follicles in the outer portion called the "cortex", which contains the lymphoid follicles, and an inner portion called "medulla", which is surrounded by the cortex on all sides except for a portion known as the "hilum". The hilum presents as a depression on the surface of the lymph node, which makes the otherwise spherical or ovoid lymph node bean-shaped. The efferent lymph vessel directly emerges from the lymph node here. The arteries and veins supplying the lymph node with blood enter and exit through the hilum.

Lymph follicles are a dense collection of lymphocytes, the number, size and configuration of which change in accordance with the functional state of the lymph node. For example, the follicles expand significantly upon encountering a foreign antigen. The selection of B cells occurs in the germinal center of the lymph nodes.

Lymph nodes are particularly numerous in the mediastinum in the chest, neck, pelvis, axilla (armpit), inguinal (groin) region, and in association with the blood vessels of the intestines.

V. B Cell Sample Preparation

In certain embodiments, B cells may be extracted for isolation of variable region nucleic acid sequences. In other embodiments, B cells may not need to be separated from a lymphoid tissue, thus saving cost and time for B cell isolation. Without B cell separation, lymphoid tissues may be directed used to obtain a pool of antibody variable gene sequences, for example, by using antibody-specific primers or probes, such as primer or probes based on antibody constant region sequences.

In one embodiment, mature, circulating B-cells (memory cells and/or antigen secreting cells (ASCs)) in peripheral blood (for example, about or at least or up to 3, 4, 5, 6, 7, 8, 9, 10, 15, 20 ml or any ranges derivable therefrom) may be used. The circulating B cells may be separated by magnetic sorting protocols (Jackson et al., 2008; Scheid et al., 2009; Smith et al., 2009; Kwakkenbos et al., 2010) as described in the Examples. Alternatively, plasma cells which are terminally differentiated B cells that reside in the bone marrow, spleen or in secondary lymphoid organs could be isolated and used for the determination of the B cell repertoire in an individual animal or human. In particular aspects, plasma cells could be mobilized from the bone marrow into circulation, e.g., by administration of G-CSF (granulocyte colony-stimulating factor) and isolated.

ASC are terminally or near terminally differentiated B cells (including plasma cells and plasmablasts) that are demarcated by the surface markers (for example, syndecan-1). They lack surface IgM and IgD, other typical B cell surface markers (e.g., CD19) and importantly, they express the repressor Blimp-1, the transcription factor Xbp-1 and down-regulate Pax-5. Antibody secreting cells can be generated from: (i) B1 cells which produce low specificity "innate-like" IgM, (ii) from B cells that do not reside in the follicles of lymphoid organs (extrafollicular) and include marginal zone (MZ, IgM$^+$, IgD$^+$, CD27$^+$) cells which generally produce lower affinity antibodies (the latter mostly in the absence T-cell help), and finally, (iii) cells of the B2 lineage that have circulated through the lymphoid follicles. B2 cells progress to the plasma stage either directly from the germinal centers where they undergo selection for higher antigen affinity (following somatic hypermutation) or after they have first entered the memory compartment. Regardless of their precise origin, these cells express high affinity antibodies predominantly of the IgG isotype and constitute the major component of the protective immune response following challenge.

Plasma cells are typically unable to proliferate or de-differentiate back to earlier B cell lineages. Most plasma cells are short-lived and die within a few days. In contrast, a fraction of the plasma cells occupy "niches" (primarily in bone marrow) that provide an appropriate cytokine microenvironment for survival and continued antibody secretion that may last from months to years; i.e., these are the cells that produce antibodies primarily involved with protection to re-challenge and constitute the "humoral memory" immune response.

A particularly preferred site for ASC isolation is the bone marrow where a large number of plasma cells that express antibodies specific for the antigen are found. It should be noted that B cells that mature to become plasma cells and to reside in the bone marrow predominantly express high affinity IgG antibodies. Mature plasma cells in the bone marrow are selected using based on cell surface markers well known in the field, e.g., CD138$^{++}$, CXCR4$^+$ and CD45$^{-/weak}$. Mature plasma cells can also be isolated based on the high expression level of the transcription factor Blimp-1; methods for the isolation of Blimp-1$^{high}$ cells, especially from transgenic animals carrying reporter proteins linked to Blimp-1 are known in the art.

On the other hand, memory B cells are formed from activated B cells that are specific to the antigen encountered during the primary immune response. These cells are able to live for a long time, and can respond quickly following a second exposure to the same antigen. In wake of first (primary response) infection involving a particular antigen, the responding naïve (ones which have never been exposed to the antigen) cells proliferate to produce a colony of cells, most of which differentiate into the plasma cells, also called effector B cells (which produce the antibodies) and clear away with the resolution of infection, and the rest persist as the memory cells that can survive for years, or even a lifetime.

VI. Nucleic Acid Sequencing

Any sequencing methods, particularly high-throughput sequencing methods, may be used to determine one or more of the VH and VL nucleotide sequences in the B cell repertoire. For example, the nucleotide sequence of the VH and VL could be determined by 454 sequencing (Fox et al., 2009) with a universal primer and without amplification to allow accurate quantitation of the respective mRNAs. Reads longer than 300 bp may be processed for further analysis (Weinstein et al., 2009). Non-limiting examples of high-throughput sequencing technologies are described below. Methods for sequencing of paired transcripts from single cells are provided, e.g., in U.S. Pat. No. 9,708,654, which is incorporated herein by reference.

High-throughput sequencing technologies are intended to lower the cost of DNA sequencing beyond what is possible with standard dye-terminator methods. Most of such sequencing approaches use an in vitro cloning step to amplify individual DNA molecules, because their molecular detection methods are not sensitive enough for single molecule sequencing. Emulsion PCR isolates individual DNA molecules along with primer-coated beads in aqueous droplets within an oil phase. Polymerase chain reaction (PCR) then coats each bead with clonal copies of the DNA molecule followed by immobilization for later sequencing. Emulsion PCR is used in the methods by Marguilis et al. (commercialized by 454 Life Sciences), Shendure and Porreca et al. (also known as "Polony sequencing") and SOLiD sequencing, (developed by Agencourt, now Applied Biosystems). Another method for in vitro clonal amplification is bridge PCR, where fragments are amplified upon primers attached to a solid surface, used in the Illumina Genome Analyzer. The single-molecule method developed by Stephen Quake's laboratory (later commercialized by Helicos) is an exception: it uses bright fluorophores and laser excitation to detect pyrosequencing events from individual DNA molecules fixed to a surface, eliminating the need for molecular amplification.

In parallelized sequencing, DNA molecules are physically bound to a surface, and sequenced in parallel. Sequencing by synthesis, like dye-termination electrophoretic sequencing, uses a DNA polymerase to determine the base sequence. Reversible terminator methods (used by Illumina and Helicos) use reversible versions of dye-terminators, adding one nucleotide at a time, detect fluorescence at each position in real time, by repeated removal of the blocking group to allow polymerization of another nucleotide. Pyrosequencing (used by 454) also uses DNA polymerization, adding one nucleotide species at a time and detecting and quantifying the number of nucleotides added to a given location through the light emitted by the release of attached pyrophosphates.

Sequencing by ligation uses a DNA ligase to determine the target sequence. Used in the polony method and in the SOLiD technology, it uses a pool of all possible oligonucleotides of a fixed length, labeled according to the sequenced position. Oligonucleotides are annealed and ligated; the preferential ligation by DNA ligase for matching sequences results in a signal informative of the nucleotide at that position.

In microfluidic Sanger sequencing the entire thermocycling amplification of DNA fragments as well as their separation by electrophoresis is done on a single glass wafer (approximately 10 cm in diameter) thus reducing the reagent usage as well as cost.

Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identifies its sequence in the DNA being sequenced. Mass spectrometry may be used to determine mass differences between DNA fragments produced in chain-termination reactions.

DNA sequencing methods currently under development include labeling the DNA polymerase (Scheid et al., 2009), reading the sequence as a DNA strand transits through nanopores, and microscopy-based techniques, such as atomic force microscopy (AFM) or electron microscopy that are used to identify the positions of individual nucleotides within long DNA fragments (>5,000 bp) by nucleotide labeling with heavier elements (e.g., halogens) for visual detection and recording.

The inventors found that less than 105 reads for each of the VH and VL pools could be sufficient to provide information on the variable gene sequences that correspond to the most abundant antibodies found in serum.

VII. RNA Sequencing

The methods of the present disclosure allow for the repertoire of immune receptors and antibodies in an individual organism or population of cells to be determined. Particularly, the methods of the present disclosure may aid in determining pairs of polypeptide chains that make up immune receptors. B cells and T cells each express immune receptors; B cells express immunoglobulins, and T cells express T cell receptors (TCRs). Both types of immune receptors consist of two polypeptide chains. Immunoglobulins consist of variable heavy (VH) and variable light (VL) chains. TCRs are of two types: one consisting of an a and a R chain, and one consisting of a γ and a δ chain. Each of the polypeptides in an immune receptor has constant region and a variable region. Variable regions result from recombination and end joint rearrangement of gene fragments on the chromosome of a B or T cell. In B cells additional diversification of variable regions occurs by somatic hypermutation. Thus, the immune system has a large repertoire of receptors, and any given receptor pair expressed by a lymphocyte is encoded by a pair of separate, unique transcripts. Only by knowing the sequence of both transcripts in the pair can one study the receptor as a whole. Knowing the sequences of pairs of immune receptor chains expressed in a single cell is also essential to ascertaining the immune repertoire of a given individual or population of cells.

In certain embodiments, the present methods comprise separating single cells in a compartment (e.g., an emulsion microcapsule) with beads conjugated to oligonucleotides; lysing the cells; allowing mRNA transcripts released from the cells to hybridize with the oligonucleotides; performing overlap extension reverse transcriptase polymerase chain reaction to covalently link DNA from at least two transcripts derived from a single cell; and sequencing the linked DNA. In certain embodiments, the cells may be mammalian cells. In certain embodiments, the cells may be B cells, T cells, NKT cells, or cancer cells.

In other embodiments, the present disclosure provides methods comprising separating single cells in a compartment with beads conjugated to oligonucleotides; lysing the cell; allowing mRNA transcripts released from the cells to hybridize with the oligonucleotides conjugated to the beads; performing reverse transcriptase polymerase chain reaction to form at least two cDNAs from at least two transcripts derived from a single cell; and sequencing the cDNA attached to the beads.

In other aspects a system can be used to separate cells in an emulsion. For example, a system can be used wherein an aqueous fluid phase exit is disposed within an annular flowing oil phase, wherein the aqueous phase fluid comprises a suspension of cells and is dispersed within the flowing oil phase, resulting in emulsified droplets with low size dispersity comprising an aqueous suspension of cells.

In other embodiments, the present disclosure provides a composition comprising a bead, an oligonucleotide capable of binding mRNA, and two or more primers specific for a transcript of interest.

Several beads or other particles conjugated with oligonucleotides may also be captured in the microwells with the single cells according to the methods of the present disclosure. In certain embodiments, beads may comprise oligonucleotides immobilized on the surface of the beads. In other embodiments, the beads may be magnetic. In other embodiments, the beads may be coated with one or more oligonucleotides. In certain embodiments, the oligonucleotides may be a poly(T), a sequence specific for heavy chain amplification, and/or a sequence specific for light chain amplification. A dialysis membrane covers the microwells, keeping the cells and beads in the microwells while lysis reagents are dialyzed into the microwells. The lysis reagents cause the release of the cells' mRNA transcripts into the microwell with the beads. In embodiments where the oligonucleotide is poly(T), the poly(A) mRNA tails are captured by the poly(T) oligonucleotides on the beads. Thus, each bead is coated with mRNA molecules from a single cell. The beads are then pooled, washed, and resuspended in solution with reagents for overlap extension (OE) reverse transcriptase polymerase chain reaction (RT-PCR). This reaction mix includes primers designed to create a single PCR product comprising cDNA of two transcripts of interest covalently linked together. Before thermocycling, the reagent solution/bead suspension is emulsified in oil phase to create droplets with no more than one bead per droplet. The linked cDNA products of OE RT-PCR are recovered and used as a template for nested PCR, which amplifies the linked transcripts of interest. The purified products of nested PCR are then sequenced and pairing information is analyzed. In other embodiments, restriction and ligation may be used to link cDNA of multiple transcripts of interest. In other embodiments, recombination may be used to link cDNA of multiple transcripts of interest.

In another embodiment, cells are lysed in emulsion droplets containing beads for nucleic acid capture. In certain embodiments, the beads may be conjugated with oligonucleotide. In certain embodiments, the oligonucleotide may be poly(T). In other embodiments, the oligonucleotide may be a primer specific to a transcript of interest. In certain embodiments, the bead may be magnetic. An aqueous solution with a suspension of both cells and beads is emulsified into oil phase by injecting an aqueous cell/bead suspension into a fast-moving stream of oil phase. The shear forces generated by the moving oil phase create droplets as the aqueous suspension is injected into the stream, creating an emulsion with a low dispersity of droplet sizes. Each cell is in its own droplet along with several beads conjugated with oligonucleotides. The uniformity of droplet size helps to ensure that individual droplets do not contain more than one cell. Cells are then thermally lysed, and the mixture is cooled to allow the beads to capture mRNA. The emulsion is broken and the beads are collected. The beads are resuspended in a solution for emulsion OE RT-PCR to link the cDNAs of transcripts of interest together. Nested PCR and sequencing of the linked transcripts is performed according to the present disclosure. In certain embodiments, the aqueous suspension of cells comprises reverse transcription reagents. In certain other embodiments, the aqueous suspension of cells comprises at least one of polymerase chain reaction and reverse transcriptase polymerase chain reaction reagents. In other embodiments, restriction and ligation may be used to link cDNA of multiple transcripts of interest. In other embodiments, recombination may be used to link cDNA of multiple transcripts of interest.

In another embodiment, emulsion droplets which contain individual cells and RT-PCR reagents are formed by injection into a fast-moving oil phase. Thermal cycling is then performed on these droplets directly. In certain embodiments, an overlap extension reverse transcription polymerase chain reaction may be used to link cDNA of multiple transcripts of interest.

In another embodiment, cDNAs of interest from a single cell are attached via RT-PCR to beads as described below, and the transcripts on the beads are sequenced directly using high-throughput sequencing. An equal mixture of three species of functionalized oligonucleotide primers may be conjugated to functionalized beads. One of the oligonucleotides may be poly(T) to capture the poly(A) tail of mRNAs. The other two oligonucleotides may be specific primers for amplifying the transcripts of interest. Beads prepared in this way are mixed with cells in an aqueous solution, and the cell/bead suspension is emulsified so that each cell is in its own droplet along with an excess of beads. In certain embodiments an average of 55 beads may be contained in each droplet. Cells are thermally lysed, and poly(T) oligonucleotides on the beads bind mRNAs. The emulsion is broken, and beads are collected, washed, and resuspended in a solution with reagents and primers for RT-PCR that will result in amplification of the transcripts of interest in such a way that the transcripts are attached to the beads. The bead suspension is emulsified and RT-PCR is performed. The beads are collected and submitted for high-throughput sequencing, which directly sequences the two transcripts attached to the beads by initiating multiple sequence reads using at least two different primers, where each initiation primer is specific to a transcript of interest. The two transcripts are paired by bead location in the high-throughput sequencing grid, revealing sequences that are expressed together from a single cell. Sequencing can be performed, for example, on Applied Biosystem's SOLiD platform, Life Technologies' Proton Torrent, or Illumina's MiSeq or HiSeq sequencing platform. In some aspects, a polymerase for use in sequence may be a proof reading polymerase. In further aspects it can be a polymerase that to capable of both RNA-templated DNA synthesis as well as DND-templated DNA synthesis (e.g., PCR). In some aspects, a polymerase can be one of those disclosed in International PCT Patent application No. WO2017127510, which is incorporated herein by reference in its entirety Primer design for OE RT-PCR determines which transcripts of interest expressed by a given cell are linked together. For example, in certain embodiments, primers can be designed that cause the respective cDNAs from the VH and VL chain transcripts to be covalently linked together. Sequencing of the linked cDNAs reveals the VH and VL sequence pairs expressed by single cells. In other embodiments, primer sets can also be designed so that sequences of TCR pairs expressed in individual cells can be ascertained or so that it can be determined whether a population of cells co-expresses any two genes of interest.

Bias can be a significant issue in PCR reactions that use multiple amplification primers because small differences in primer efficiency generate large product disparities due to the exponential nature of PCR. One way to alleviate primer bias is by amplifying multiple genes with the same primer, which is normally not possible with a multiplex primer set. By including a common amplification region to the 5' end of multiple unique primers of interest, the common amplification region is thereby added to the 5' end of all PCR products during the first duplication event. Following the initial duplication event, amplification is achieved by priming only at the common region to reduce primer bias and allow the final PCR product distribution to remain representative of the original template distribution.

Such a common region can be exploited in various ways. One clear application is to add the common amplification primer at higher concentration and the unique primers (with 5' common region) at a low concentration, such that the majority of nucleic acid amplification occurs via the common sequence for reduced amplification bias. Another application is the surface-based capture of amplification products, for example to capture PCR product onto a microbead during emulsion PCR. If the common sequence oligonucleotides are immobilized onto a bead surface, the PCR products of interest will become covalently linked to the bead during amplification. In this way, a widely diverse set of transcripts can be captured onto a surface using a single immobilized oligonucleotide sequence.

For example, two different common regions may be immobilized onto a bead surface at equal concentration (e.g., one common sequence for heavy chain, and a different common sequence for light chain). Following PCR amplification, the bead will be coated with approximately 50% heavy chain amplification product, and 50% light chain amplification product. This balance between heavy and light chain representation on the bead surface helps ensure sufficient signal from both heavy and light chains when the bead is submitted to high throughput sequencing.

Accordingly, in certain embodiments, the present disclosure provides methods comprising adding a common sequence to the 5' region of two or more oligonucleotides that are specific to a set of gene targets; and performing nucleic acid amplification of the set of gene targets by priming the common sequence. In certain embodiments, the common sequence n is immobilized onto a surface. In other embodiments, the common sequence may be used to capture amplification products.

The methods of the present disclosure allow for information regarding multiple transcripts expressed from a single cell to be obtained. In certain embodiments, probabilistic analyses may be used to identify native pairs with read counts or frequencies above non-native pair read counts or frequencies. The information may be used, for example, in studying gene co-expression patterns in different populations of cancer cells. In certain embodiments, therapies may be tailored based on the expression information obtained using the methods of the present disclosure. Other embodiments may focus on discovery of new lymphocyte receptors.

VIII. Sequence Abundancy Determination

Bioinformatic methods for the automated analysis of sequencing results such as Illumina MiSeq reads, statistical sequencing error analysis and finally identification and classification of CDRs, especially of CDR3, the most hypervariable region in antibodies have been developed by the inventors.

In certain embodiments, for example to account for sequencing/PCR uncertainties, antibody sequences, could be grouped into families, with each family consisting of all the sequences differing by several nucleotides or amino acids.

For example, the abundancy level of antibody variable region sequences may be based on the CDR3 sequences as identifiers. The sequences for determination of a level of abundancy may be a family including an identical CDR3 sequence (amino acid sequence or nucleic acid sequence) and a CDR3 sequence having at least 80% homology, for example 85, 90, 95, 96, 97, 98 or 99% homology therewith. Sequence homology is as determined using the Usearch clustering algorithms (Edgar, 2010). For example, the sequences occurring in total at a relative level of abundancy represented by a frequency at least 1 percent in the set of sequences may be a combination of the CDR3 sequences or a sequence having 1 or 2 amino acid changes therefrom. For example, a first sequence may occur at a frequency of 0.7 percent, and second, third and fourth sequences each having a single amino acid change therefrom each occur at a frequency of 0.1%—the total occurrence in abundancy is therefore 1.0% and the dominant antibody sequence (occurring at a frequency of 0.7%) is therefore a candidate CDR3 sequence that could be used for antibody generation/characterization.

IX. Quantitative Serum Antibody Analysis

To identify a pool of abundant amino acid sequences of CDR regions, especially CDR3 regions of circulating antibodies, MS shotgun proteomics or protein sequencing methods may be used to determine the amino acid sequences.

Any protein sequencing methods determining the amino acid sequences of its constituent peptides may be used. The two major direct methods of protein sequencing are mass spectrometry and the Edman degradation reaction. It is also possible to generate an amino acid sequence from the DNA or mRNA sequence encoding the protein, if this is known. However, there are also a number of other reactions which can be used to gain more limited information about protein sequences and can be used as preliminaries to the aforementioned methods of sequencing or to overcome specific inadequacies within them.

For example, shotgun proteomic strategy based on digesting proteins into peptides and sequencing them using tandem mass spectrometry and automated database searching could be the method of choice for identifying serum antibody sequences. "Shotgun proteomics" refers to the direct analysis of complex protein mixtures to rapidly generate a global profile of the protein complement within the mixture. This approach has been facilitated by the use of multidimensional protein identification technology (MudPIT), which incorporates multidimensional high-pressure liquid chromatography (LC/LC), tandem mass spectrometry (MS/MS) and database-searching algorithms.

A. IgG Fractionation

Ig proteins of a particular class could be isolated, for example, by affinity chromatography using protein A (or anti-IgA and anti-IgM antibodies for affinity purification of the other major Ig classes).

In certain aspects, antibodies or antibody fragments such as FAB fraction from digestion of purified Igs with papain and FAB purification, could be affinity enriched for binding to desired antigen or pathogen (e.g., a cancer cell, a tumor antigen, or an infection agent), or host tissue for the isolation of antibodies suspected to have a role in autoimmunity. Antibodies may be eluted under denaturing conditions. In further embodiments, several fractions or pools of serum-derived FABs could be generated, including those that are: (a) enriched for antigen, (b) enriched for host tissue and (c) antibodies with unrelated or unknown specificities.

B. Proteolytic Fragmentation

For quantitative shotgun proteomics mass spectrometry analysis, antibodies or antibody fragments such as FAB could be digested using proteases that cleave after amino acids/amino acid pairs that are under-represented in CDR3 but present in the adjacent framework regions. The appropriate proteases for proteomic processing may be identified by bioinformatics analysis of the V gene sequence database.

In one example the FAB fractions are subjected to proteolysis with sequencing grade trypsin (Sigma) at 37° C. for 4 hr. As an alternate method, a combination of the proteases GluC (NEB) and LysC (Sigma) could be used in place of trypsin to generate a distinct set of proteolytic peptides that in computational tests provide better coverage of the CDR3s (i.e. so that cleavage occurs at positions flanking the CDR3s and therefore peptides with intact CDR3s are produced).

In certain embodiments, CDR3 peptides could be enriched from unrelated peptides via specific conjugation of the unique Cys at the end of the CDR3 sequence with a thiol specific reagent that allows the purification of such peptides.

The inventors have developed protocols that deploy a combination of appropriate proteases for peptide generation and Cys specific pull down of thiol containing CDR3 peptides which result in a peptide mixture comprising of at least 30% CDR3 peptide sequences. In one example, CDR3 peptides are enriched via reversible thiol specific biotinylation. In another example, CDR3 peptides are reacted with special chromophores that allow their specific excitation and detection during MS analysis. As the CDR3 peptides almost universally (>99%) contain cysteine, a biotinylated thiol-specific cross-linking agent is used to affinity isolate these peptides for mass spectral analysis thus greatly simplifying the complexity of the spectra.

C. Shotgun MS (Mass Spectrometry) Proteomics

In certain exemplary aspects, the peptides of antibody molecules could be resolved by reverse phase chromatography and in-line nanoelectrospray ionization/high-resolution tandem mass spectrometry, using well-established protocols (Ong and Mann, 2005; Pandey and Mann, 2000; Shevchenko et al., 1996; Hunt et al., 1986; Link et al., 1999; Washburn et al., 2001; Lu et al., 2007) and Fourier-transform LTQ-Orbitrap mass spectrometry (Hu et al., 2005) to collect hundreds of thousands of tandem mass spectra from CDR3 and other FAB-derived peptides.

For example, peptides are separated on a reverse phase Zorbax C-18 column (Agilent) running an elution gradient from 5% to 38% acetonitrile, 0.1% formic acid. Peptides were eluted directly into an LTQ-Orbitrap mass spectrometer (Thermo Scientific) by nano-electrospray ionization. Data-dependant ion selection could be enabled, with parent ion mass spectra (MS1) collected at 100k resolution. Ions with known charge >+1 may be selected for CID fragmentation spectral analysis (MS2) in order to decrease intensity, with a maximum of 12 parent ions selected per MS1 cycle. Dynamic exclusion is activated, with ions selected for MS2 twice within 30 sec. Ions identified in an LC-MS/MS run as corresponding to peptides from the constant regions of the heavy and light chains may be excluded from data-dependent selection in subsequent experiments in order to increase selection of peptides from the variable region.

D. MS Proteomic Data Analysis

The variable gene sequencing data from B cells of the same subject are employed to supplement the protein sequence database for interpreting peptide mass spectra in shotgun proteolysis (Marcotte, 2007). With the aid of the sample-specific sequence database, we identify CDR3 peptides from the tandem mass spectra (controlling for false discovery rate using standard methods (Keller et al., 2002; Nesvizhskii et al., 2009).

Several recent advances in shotgun proteomics enable protein quantification to ~2-fold absolute accuracy without introducing additional requirements for isotope labels or internal calibrant peptides (Lu et al., 2007; Malmstrom et al., 2009; Silva et al., 2006a; Vogel and Marcotte, 2008; Ishihama et al., 2005; Liu et al., 2004). Among these approaches, two are well-suited to quantification of individual IgGs: the APEX approach is based upon weighted counts of tandem mass spectra affiliated with a protein (the weighting incorporates machine learning estimates of peptide observability (Lu et al., 2007; Vogel, 2008), and the average ion intensity approach, based on mass spectrometry ion chromatogram peak volumes (Silva et al., 2006a). For example, both methods could be employed to measure abundances of each of the identified antigen-specific IgGs in the serum-containing sample. Combinations (Malmstrom et al., 2009) and single peptide quantitation methods could also be used as alternatives. Algorithms for subtraction of non-CDR3 peptides could be used. On the basis of these measured abundances, at least the 50 or 100 most highly abundant $V_H$ and $V_L$ proteins in the sample could be rank-ordered.

For example, sample-specific protein sequence databases are created from high-throughput V region cDNA transcript data. $V_H$ and $V_L$ gene represented by >8 reads by 454 sequencing are compiled into a database which in turn is added to a concatenated forward/reversed-sequence protein-coding database. The LC-MS/MS data is searched against this database using the Sequest search algorithm as part of the Bioworks software package (Thermo Scientific). Filters are applied to ensure high confidence peptide identifications as follows: $\Delta CN \geq 0.250$; XCorr=2.0, 2.5, and 3.0 for +2, +3, and $\geq$+4 charge; and accuracy $\leq$10.0 ppm.

In certain embodiments, the amino acid sequence analysis coupled with the information various V gene pools of different B cell source (e.g., the particular organ-specific ASC population that expresses $V_H$ and $V_L$ genes whose products are found in serum) could be employed to identify whether a particular serum antibody originated preferentially in the bone marrow, in secondary lymphoid tissues (as is likely to be the case early in the immune response), or in the case of persistent infection, possibly in tertiary lymphoid tissues. The possibility that a particular antibody is secreted by plasma cells that have migrated to different tissues could also be addressed. At a systems level the inventors could employ this information to estimate the contribution of different compartments to humoral immunity in a quantitative fashion and could generate antibody or antibody fragments involved in different stage of immune response.

X. Antibody Generation and Characterization

Certain embodiments described above lead to the identification and quantitation of abundant serum antibodies of interest or the most abundant variable region sequences in B cells or in a selected lymphoid tissue. Such information may be used to develop antibody or antibody fragments that have desired binding affinity or antigen response, such as to cancer-specific antigens. In certain aspects, their binding specificities or therapeutic utility could be evaluated. For example, antibody or antibody fragments which are cytotoxic towards cancer cells could be generated from the abundant serum polyclonal antibody pool. In further embodiments, antibody or antibody specific fragments that are specific for the antigen used to immunize any animal may be provided by analyzing sequence and abundance information of variable region nucleic acids in B cells or directly from lymphoid tissues.

In certain embodiments, a cancer-specific antibody, antigen receptor or a fragment thereof that binds to at least a portion of a cancer-specific protein or antigen and inhibits cancer specific signaling and cancer cell proliferation are contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand.

A. Gene Synthesis for Antibody Generation

To generate antibody or antibody fragments with desired binding specificity or property, the V genes could be synthesized, assembled into FAB or IgG and expressed. $V_H$ and $V_L$ genes may be generated by high throughput gene synthesis based on the sequence information obtained by the methods described above.

For example, automated gene synthesis could be used. Briefly, gene fragments (lengths from 200 to 500 nucleotides) are generated using inside-out nucleation PCR reactions under carefully controlled conditions to ensure construction of the desired final fragment. Subsequently stitch-overlap extension PCR is used to synthesize the gene of interest. The design of these fragments and relevant overlaps is automated, with oligonucleotide synthesizer worklists and robot operation scripts for synthesis and assembly. With the current configuration, a throughput of 48 kilobases is attained per robotic assembly run (4 hours). Alignment of sequences so as to maintain maximal conservation and subsequent "padding" of the sequences at either end to maintain identical length permits the use of a generic overlapping oligonucleotide assembly strategy and also ensures the most oligonucleotide re-use. Currently throughput stands at 50 $V_H$ and 50 $V_L$ genes (i.e. >38,000 bp of DNA) synthesized and validated for correct ORF by one researcher within a week and at a reagent cost <$2,000.

B. Antibody Expression

In further aspects, the synthesized $V_H$ and $V_L$ genes may be inserted into appropriate vectors for expression, for example, as FABs in *E. coli* or as full length IgGs by transient transfection of HEK293 cells.

Binding between candidate antibody or antibody fragments and antigen could be then evaluated by any methods for binding detection and quantification, particularly ELISA. For example, cancer specific antibodies or antibody fragments could be characterized by cancer and host cell binding by fluorescence-activated cell sorting (FACS) following fluorescent labeling of antibodies.

Antibodies according to certain aspects of the invention may be labeled with a detectable label or may be conjugated with an effector molecule, for example a drug e.g., an antibacterial agent or a toxin or an enzyme, using conventional procedures and the invention extends to such labeled antibodies or antibody conjugates.

Antibodies usable or produced in the present invention, may be a whole antibody or an antigen binding fragment thereof and may in general belong to any immunoglobulin class. Thus, for example, it may be an IgA or an IgG antibody. The antibody or fragment may be of animal, for example, mammalian origin and may be for example of murine, rat, sheep or human origin. Preferably, it may be a recombinant antibody fragment, i.e., an antibody or antibody fragment which has been produced using recombinant DNA techniques. Such recombination antibody fragment may comprise prevalent CDR or variable domain sequences identified as above.

XI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 1B:
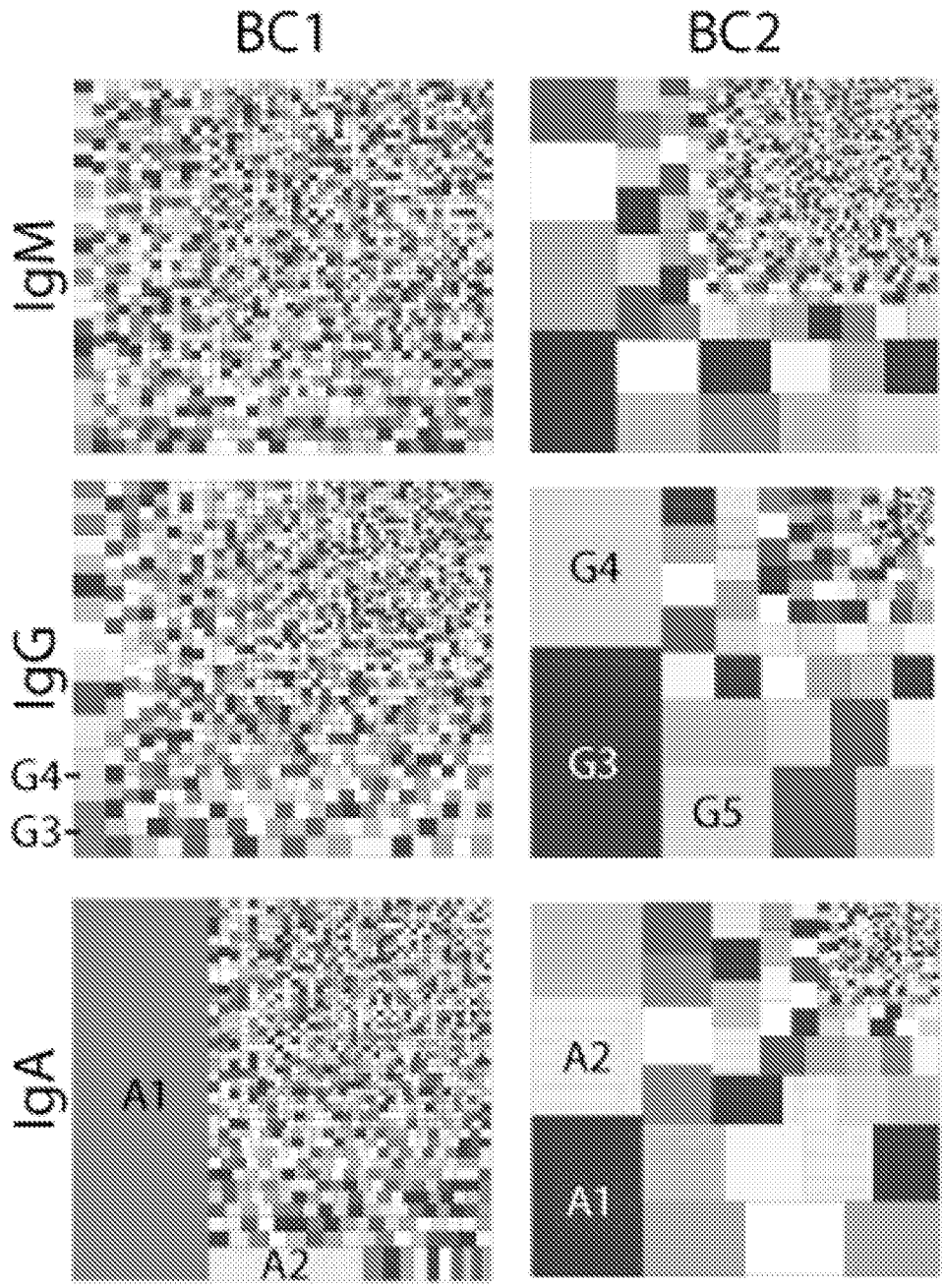
Figure 1C:
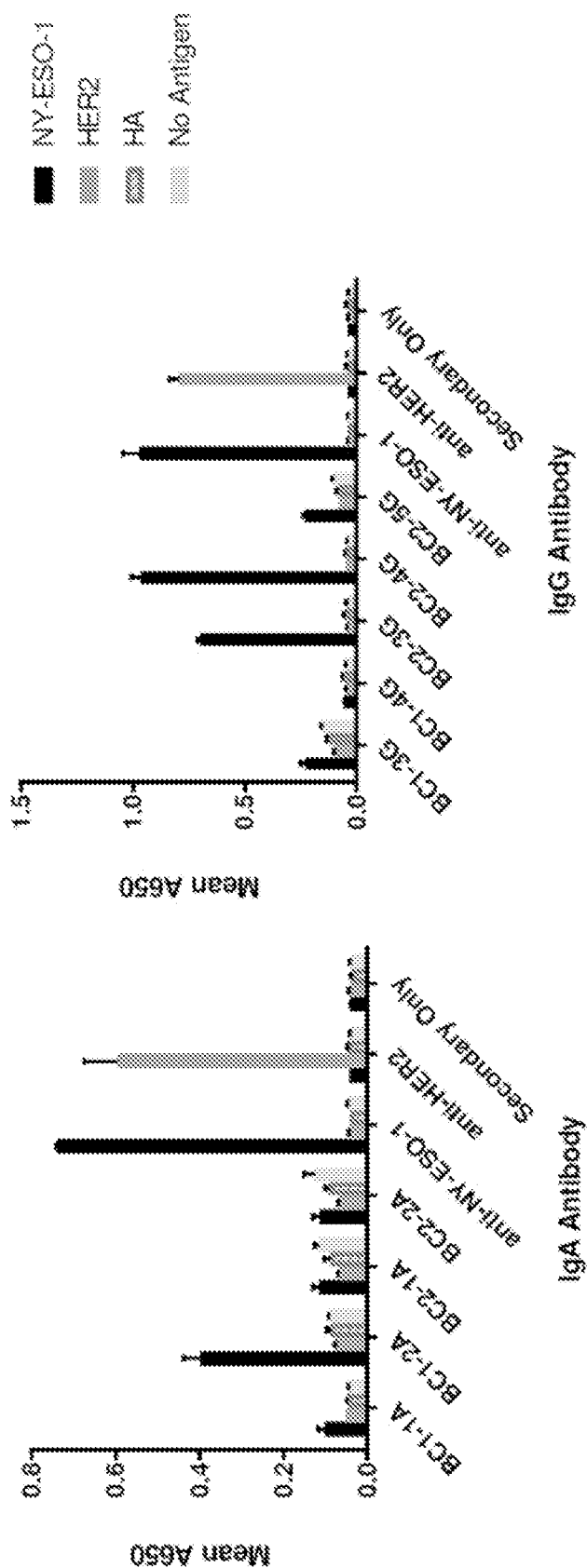

Example 1—Identification of Antibodies from the Sentinel Lymph Node B-Cells of Blood and Breast Cancer Patients Isolation and Preparation of Tissues and Plasma. Newly diagnosed patients with breast cancer were evaluated for elevated antibody titers to a small panel of tumor-related antigens. Blood, a portion of the SN, and a portion of the primary breast tumor were collected at the time of surgery. The blood plasma was measured for elevated antibody titers to HER2, MUC-1, p53, and NY-ESO-1. Hemagglutinin Flu B (HA) protein antigen was included as a positive control. Two breast cancer patients were identified, BC-1 and BC-2, with elevated blood plasma titers to NY-ESO-1 antigen (FIG. 1C). Freshly harvested sentinel lymph nodes (SNs) were minced in cold RPMI media with 10% FBS between 40 μm nylon mesh, and pressed with a rubber plunger to isolate mononuclear cells. Cell count and viability was determined by trypan blue exclusion. Cells were cryopreserved in 90% fetal bovine serum (Sigma)/10% dimethyl sulfoxide. Blood was collected in Monoject™ EDTA coated blood collection tubes (Covidien) at time of surgery and then transferred to a centrifuge tube. The plasma layer was collected by centrifugation at 1000×g for 10 min, and stored in aliquots at −20° C.

Antibody cloning, expression, and purification. Selected antibody sequences were purchased as gBlocks gene fragments (Integrated DNA Technologies) and cloned into a customized pcDNA3.4 vector (Invitrogen) containing human IgG1 or IgA1 Fc regions. VH and VL plasmids were transfected into 30 mL cultures of Expi293F cells (Invitrogen) at a 1:2 ratio and incubated at 37° C. and 8% CO2 for 7 days. The supernatant containing secreted antibodies was collected following centrifugation (1000 g for 10 min at 4° C.), neutralized, and filtered. Antibodies were isolated using Protein G Plus agarose (IgG; Pierce Thermo Fisher Scientific) or Peptide M agarose (IgA; Invitrogen) affinity chromatography, washed with 20 column volumes of PBS, eluted with 100 mM glycine-HCl pH 2.7, and immediately neutralized with 1 M Tris-HCl pH 8.0. The antibodies were then concentrated and buffer exchanged into PBS using 10,000 MWCO Vivaspin centrifugal spin columns (Sartorius).

Binding analysis of Plasma and Purified antibodies. Flat-bottom 96-well MaxiSorp plates (Nunc) were prepared by coating with antigens (5 μg/ml) in phosphate buffered saline (PBS), or with PBS alone, at 4° C. overnight. Human antigens used include: the extracellular domain of ErbB2 (HER2; Creative Biomolecules, Inc.), MUC-1 (partial ORF 315-420 aa; Abnova), Hemagglutinin (HA; FluB/Florida/4/2006; eEnzyme), NY-ESO-1 (ThermoFisher or RayBiotech Inc.), and p53 (Sigma-Aldrich). Wells were washed with Tris-buffered saline (TBS) containing 0.1% Tween-20 (TBST-0.1%), and nonspecific binding sites were blocked for 2 hours with 1% bovine serum albumin (BSA; Sigma-Aldrich). Diluted plasma (1:2000 in PBS)(FIG. 1A) or purified human antibodies (FIG. 1C) were incubated in antigen coated wells for 2 h at room temperature. Human anti-HER2 (trastuzumab; Genentech Inc.) and mouse anti-NY-ESO-1 monoclonal antibody (E978; Thermo Fisher) were used as positive controls. After washing the plates, antigen-reactive antibodies were reacted with mouse anti-human IgG (Fc)-horseradish peroxidase (HRP; 1:5000 dilution; Southern Biotech) or goat anti-mouse IgG (H+L)-HRP in Casein-TBS Blocker (Thermo Fisher) with gentle shaking for 1 hour. After washing 5 times with TBST-0.1% and once with TBS, the bound antibody was detected with 3,3',5,5'-tetramethylbenzidine soluble substrate (TMB; Millipore) by monitoring the formation of blue-colored product at 650 nm for 15 min using a Synergy HT plate reader (BioTek Instruments, Inc.). BC1 and BC2 cell lines were selected for further characterization based on the presence of anti-NY-ESO-1 antibodies (FIG. 1A).

Surface plasmon resonance. NY-ESO-1 (RayBiotech Inc.) was immobilized on CM5 sensor chips by amine coupling, as recommended by the manufacturer (GE Healthcare). Binding experiments were performed in HBS-EP buffer (10 mM HEPES pH 7.4, 150 mM NaCl, 3.4 mM EDTA, and 0.005% P20 surfactant). Serially diluted antibodies were injected at a flow rate of 30 μL/min for 60 s with a dissociation time of 5 min. The chip was regenerated after each run by sequential injection of 10 mM glycine, pH 3, and 500 mM arginine, pH 8 for 1 min each. For each run, a bovine serum albumin (BSA)-coupled surface was used to subtract non-specific receptor binding. The $K_D$ of each monoclonal antibody was calculated by fitting 2:1 bivalent analyte models (A+2B<->AB+B<->AB2) to the data using BIAevaluation 3.2 software (GE Healthcare) in accordance with previously reported analyses (Lee et al., 2017) and averaged from three independent experiments. Monoclonal antibodies from BC2-3G and BC2-4G lineages displayed nM affinity for binding to NY-ESO-1 as determined by SPR analysis (FIG. 2E, FIG. 5A-E), with the apparent affinities varying greatly between the lineages (FIG. 5).

Immunofluorescence microscopy of tumor NY-ESO-1. Frozen sections (6 μm thick) mounted onto uncoated glass slides were fixed in 4% paraformaldehyde (Electron Microscopy Sciences) in PBS, rinsed in PBS, and blocked in 10% normal goat serum (Jackson Immuno Research) diluted with PBS containing 5.0% BSA and 0.1% Triton X-100. All washes were performed with PBS containing 5% BSA. Tumor NY-ESO-1 was detected with 2.5 μg/mL anti-NY-ESO-1 monoclonal antibody (Invitrogen), followed by 4 μg/mL Alexa fluor 555-conjugated goat anti-mouse-IgG (H+L) (Invitrogen). Representative images were obtained on the 510 META confocal scanning laser microscope (Zeiss). Primary tumor tissue in patients BC1 and BC2 was confirmed to have positive NY-ESO-1 expression by immunofluorescence staining.

Epitope mapping for a NY-ESO-1-binding antibody. The PEPperMAP® Epitope Mapping of human IgG1 monoclonal antibody BC2-3G(4) was performed against NY-ESO-1/CTAG1B translated into linear overlapping 15 amino acid peptides with a peptide-peptide overlap of 14 amino acids for high-resolution epitope data (see FIG. 6). The resulting NY-ESO-1/CTAG1B peptide microarrays were incubated with the human IgG1 monoclonal antibody at concentrations of 1 μg/ml (lower plot) and 10 μg/ml (upper plot) in incubation buffer followed by staining with secondary and control antibodies as well as read-out with a LI-COR Odyssey Imaging System. Quantification of spot intensities and peptide annotation were done with PepSlide® Analyzer. Pre-staining of a NY-ESO-1/CTAG1B peptide microarray copy with secondary and control antibodies antibody did not show any background interaction with the antigen-derived peptides that could interfere with the main assays. Incubation of NY-ESO-1/CTAG1B peptide microarray copies with human IgG1 monoclonal antibody BC2-3G(4) showed a weak to moderate and clear monoclonal antibody response with high signal-to-noise ratios against an epitope-like spot pattern formed by adjacent peptides with the consensus motif TPMEAELARR.

Example 2—Interrogation of SN B Cells by BCR-Seq

BCR-seq library preparation and sequencing. SN cells were isolated as in Example 1. B cells were purified from isolated SN cells using the human B cell enrichment kit (StemCell Technologies). A custom-designed axisymmetric flow focusing device was used to coemulsify single cells with lysis buffer (100 mM Tris pH 7.5, 500 mM LiCl, 10 mM EDTA, 1% lithium dodecyl sulfate, and 5 mM DTT) and oligo d(T)$_{25}$ magnetic beads (New England Biolabs).

The magnetic beads were washed, resuspended in a customized high-yield RT-PCR solution (Table 1).

TABLE 1

| Component | Amount per reaction (μL) | Final Amount |
|---|---|---|
| Common primer mix (10 μM each) | 115 | 400 nM each |
| Constant region multiplex primer mix (10 μM each) | 11.5 | 40 nM each |
| VH FR1 OE Multiplex primer mix (12.5 μM each) | 9.2 | 40 nM each |
| VL FR1 OE Multiplex primer mix (7.7 μM each) | 14.9 | 40 nM each |
| Ultrapure BSA (50 mg/ml) | 29 | 1.45 mg |
| SUPERase•In RNase inhibitor (20 U/μl) | 115 | 2300 U |
| dNTPs (10 mM each) | 57.5 | 200 μM each |
| Betaine (5M) | 575 | 1M |
| RTX Enzyme buffer (10X)$^a$ | 287.5 | 1 X |
| RTX Enzyme | 57.5 | 10 μg |
| H$_2$O | Fill to 2,875 | |

The resuspended beads were then emulsified, and subjected to overlap-extension RT-PCR utilizing reverse transcription xenopolymerase (RTX; see International PCT Patent application No. WO2017127510, which is incorporated herein by reference in its entirety) under the following conditions: 30 min at 68° C. followed by 2 min at 94° C.; 25 cycles of 94° C. for 30 s, 60° C. for 30 s, 68° C. for 2 min; 68° C. for 7 min; held at 4° C. The RT-PCR solution contained a multiplex set of VH and VL primers (Table 2) designed to physically stitch the two antibody chains into a single amplicon.

TABLE 2

Primers for overlap extension RT-PCR reaction

Common Mix

| IGH | CGCAGTAGCGGTAAACGGC |
| | (SEQ ID NO: 45) |
| IGL | GCGGATAACAATTTCACACAGG |
| | (SEQ ID NO: 46) |

VII FR1 OE Multiplex Mix

| hVH1 | TATTCCCATCGCGGCGCCAGGTCCAGCTKGTRCAGTCTGG |
| | (SEQ ID NO: 47) |
| hVH157 | TATTCCCATCGCGGCGCCAGGTGCAGCTGGTGSARTCTGG |
| | (SEQ ID NO: 48) |

TABLE 2-continued

Primers for overlap extension RT-PCR reaction

| | |
|---|---|
| hVH2 | TATTCCCATCGCGGCGCCAGRTCACCTTGAAGGAGTCTG (SEQ ID NO: 49) |
| hVH3 | TATTCCCATCGCGGCGCGAGGTGCAGCTGKTGGAGWCY (SEQ ID NO: 50) |
| hVH4 | TATTCCCATCGCGGCGCCAGGTGCAGCTGCAGGAGTCSG (SEQ ID NO: 51) |
| hVH4-DP63 | TATTCCCATCGCGGCGCCAGGTGCAGCTACAGCAGTGGG (SEQ ID NO: 52) |
| hVH6 | TATTCCCATCGCGGCGCCAGGTACAGCTGCAGCAGTCA (SEQ ID NO: 53) |
| hVH3N | TATTCCCATCGCGGCGCTCAACACAACGGTTCCCAGTTA (SEQ ID NO: 54) |

FR1 VL Multiplex

| | |
|---|---|
| hVK1 | GCGCCGCGATGGGAATAGCTAGCCGACATCCRGDTGACCCAGTCTCC (SEQ ID NO: 55) |
| hVK2 | GCGCCGCGATGGGAATAGCTAGCCGATATTGTGMTGACBCAGWCTCC (SEQ ID NO: 56) |
| hVK3 | GCGCCGCGATGGGAATAGCTAGCCGAAATTGTRWTGACRCAGTCTCC (SEQ ID NO: 57) |
| hVK5 | GCGCCGCGATGGGAATAGCTAGCCGAAACGACACTCACGCAGTCTC (SEQ ID NO: 58) |
| hVL1 | GCGCCGCGATGGGAATAGCTAGCCCAGTCTGTSBTGACGCAGCCGCC (SEQ ID NO: 59) |
| hVL1459 | GCGCCGCGATGGGAATAGCTAGCCCAGCCTGTGCTGACTCARYC (SEQ ID NO: 60) |
| hVL15910 | GCGCCGCGATGGGAATAGCTAGCCCAGCCWGKGCTGACTCAGCCMCC (SEQ ID NO: 61) |
| hVL2 | GCGCCGCGATGGGAATAGCTAGCCCAGTCTGYYCTGAYTCAGCCT (SEQ ID NO: 62) |
| hVL3 | GCGCCGCGATGGGAATAGCTAGCCTCCTATGWGCTGACWCAGCCAA (SEQ ID NO: 63) |
| hVL-DPL16 | GCGCCGCGATGGGAATAGCTAGCCTCCTCTGAGCTGASTCAGGASCC (SEQ ID NO: 64) |
| hVL3-38 | GCGCCGCGATGGGAATAGCTAGCCTCCTATGAGCTGAYRCAGCYACC (SEQ ID NO: 65) |
| hVL6 | GCGCCGCGATGGGAATAGCTAGCCAATTTTATGCTGACTCAGCCCC (SEQ ID NO: 66) |
| hVL78 | GCGCCGCGATGGGAATAGCTAGCCCAGDCTGTGGTGACYCAGGAGCC (SEQ ID NO: 67) |

Constant Region Multiplex

| | |
|---|---|
| hIgM | CGCAGTAGCGGTAAACGGCCGACGGGGAATTCTCACAGGAGACGAGGGGGAAA (SEQ ID NO: 68) |
| hIgG | CGCAGTAGCGGTAAACGGCGGAGSAGGGYGCCAGGGGGAAGAC (SEQ ID NO: 69) |
| hIgA | CGCAGTAGCGGTAAACGGCGCTCAGCGGGAAGACCTTGGGGCTGG (SEQ ID NO: 70) |
| hIgLC | GCGGATAACAATTTCACACAGGTTGRAGCTCCTCAGAGGAGGGYGGGAA (SEQ ID NO: 71) |
| MgKC | GCGGATAACAATTTCACACAGGCTGCTCATCAGATGGCGGGAAGATGAAGACAGATGGTGCAG (SEQ ID NO: 72 |

Nested

| | |
|---|---|
| hIgG | ATGGGCCCTGSGATGGGCCCTTGGTGGARGC (SEQ ID NO: 73) |
| hIgM | ATGGGCCCTGGGTTGGGGCGGATGCACTCC (SEQ ID NO: 74) |
| hIgA | ATGGGCCCTGCTTGGGGCTGGTCGGGGATG (SEQ ID NO: 75) |
| hIgKC | GTGCGGCCGCAGATGGTGCAGCCACAGTTC (SEQ ID NO: 76) |
| hIgLC | GTGCGGCCGCGAGGGYGGGAACAGAGTGAC (SEQ ID NO: 77) |

Bolded basepairs represent the linking sequence between the VH and VL primers.

Bolded basepairs represent the linking sequence between the VH and VL primers.

The resultant VH:VL DNA amplicon was isolated from the emulsions, amplified using nested PCR, and then split into three libraries for paired-end sequencing using an Illumina MiSeq. The full length VH and VL amplicon was sequenced in order to maintain the CDR-H3:CDR-L3 paired information, While the separate VH and VL libraries were sequenced to provide phylogenetic data on the full length variable region.

Bioinformatic analysis of the VH:VL repertoire. Raw 2×300 MiSeq reads from the paired VH:VL library were trimmed based on sequence quality using Trimmomatic (Bolger et al., 2014) and submitted to MiXCR for gene annotation (Bolotin et al., 2015). Productive VH and VL reads were split by isotype and paired using a custom python script. Sequences with ≥2 reads were grouped into lineages by clustering the CDR-H3 region on 90% nucleotide identity. 100 repetitions of random sampling and lineage enumeration were performed and the number of Illumina reads for each lineage was transformed into a frequency to generate mosaic plots for each isotype, where the area of each square is proportional to the number of sequencing reads belonging to each lineage (FIG. 1B) (Plotly Technologies Inc., 2015). 17,855 lineages were identified from the B cells isolated from BC1 SN from about 474,000 productive VH:VL sequences from 1.7 million raw reads, and 8,678 lineages from the B cells isolated from BC2 SN from about 512,000 productive VH:VL sequences from 1.7 million raw reads. The number of IgG and IgA lineages relative to IgM averaged 77% and 83% for BC1, respectively, and 27% and 15% for BC2. This polarization, which was most pronounced in BC2, suggests that the class-switched B cells from the SN are less diverse because they are experiencing antigen-driven clonal expansion. This visualization strategy may help identify anticancer antibody lineages that experienced affinity selection in the SN germinal centers in response to chronic stimulation by tumor antigens.

Phylogenetic analysis of the variable regions. Raw MiSeq reads were stitched into full length variable regions using PEAR (Zhang et al., 2014), quality filtered, and annotated by MiXCR (Bolotin et al., 2015). Lineages of interest were identified by 90% CDR-H3 nucleotide identity, and their members were clustered on the full length nucleotide sequence at 97% identity to reduce PCR and sequencing error. The sequences were aligned by MAFFT (Katoh et al., 2002) and organized into maximum likelihood phylogenetic trees based on the variable region using RAxML (Stamatakis, 2014). Sub-lineages were defined on the basis of the CDR-H3 amino acid sequence.

Figure 2A:
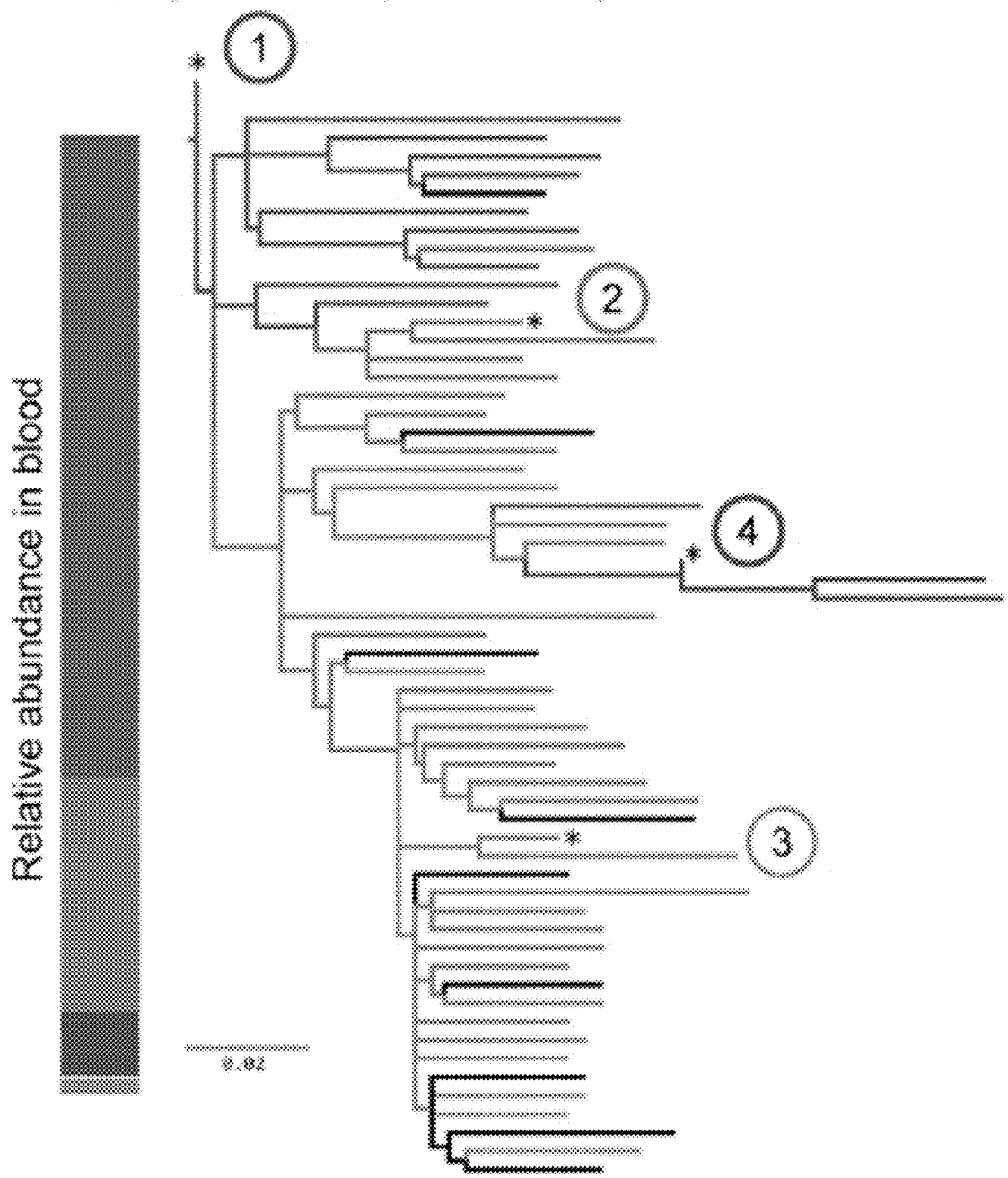
FIG. 2: Antigen-driven affinity maturation of a B-cell lineage. (A) Maximum likelihood phylogram for sample BC2 IgG 3G. Sub-lineages are defined by different CDR-H3 amino acid sequences. Black nodes represent CDR-H3 sequences that do not exactly match one of the primary sub-lineage CDR-H3s. Side bar represents the relative abundancies of each sub-lineage detected in blood. (B) Table indicating the pairing specificity of CDR-H3 to CDR-L3 across dominant lineage members and affinity for NY-ESO-1. (CARDLGIAAAGDFDYW, SEQ ID NO: 6; CARDLGPAAAADFDYW, SEQ ID NO: 7; CARDLGVTAAADFDFW, SEQ ID NO: 8; CARDLGLAAAADFDFW, SEQ ID NO: 9; CHQGSNWPTF, SEQ ID NO: 13; CHQHFNWPTF, SEQ ID NO: 14; CHQHRSWPTF, SEQ ID NO: 15) Representative (C) VH and (D) VL sequences for each sub-lineage denoted by an asterisk in (A). CDR1, CDR2, and CDR3 regions are underlined. (In C, VH6-1=SEQ ID NO: 78; in D, VK3-11=SEQ ID NO: 79) (E) Relationship between the number of somatic mutations in the VH and VL genes and $K_D$ as determined by SPR for lineage members 1, 2, 3, and 4. $K_D$ values are shown in Table B. (F) Underlined sequences represent peptides detected by LC-MS/MS that map to sub-lineage 1. Only the CDR-H3 peptide was used to quantify relative abundancies between lineages. (SEQ ID NO: 80)
Figure 3A:
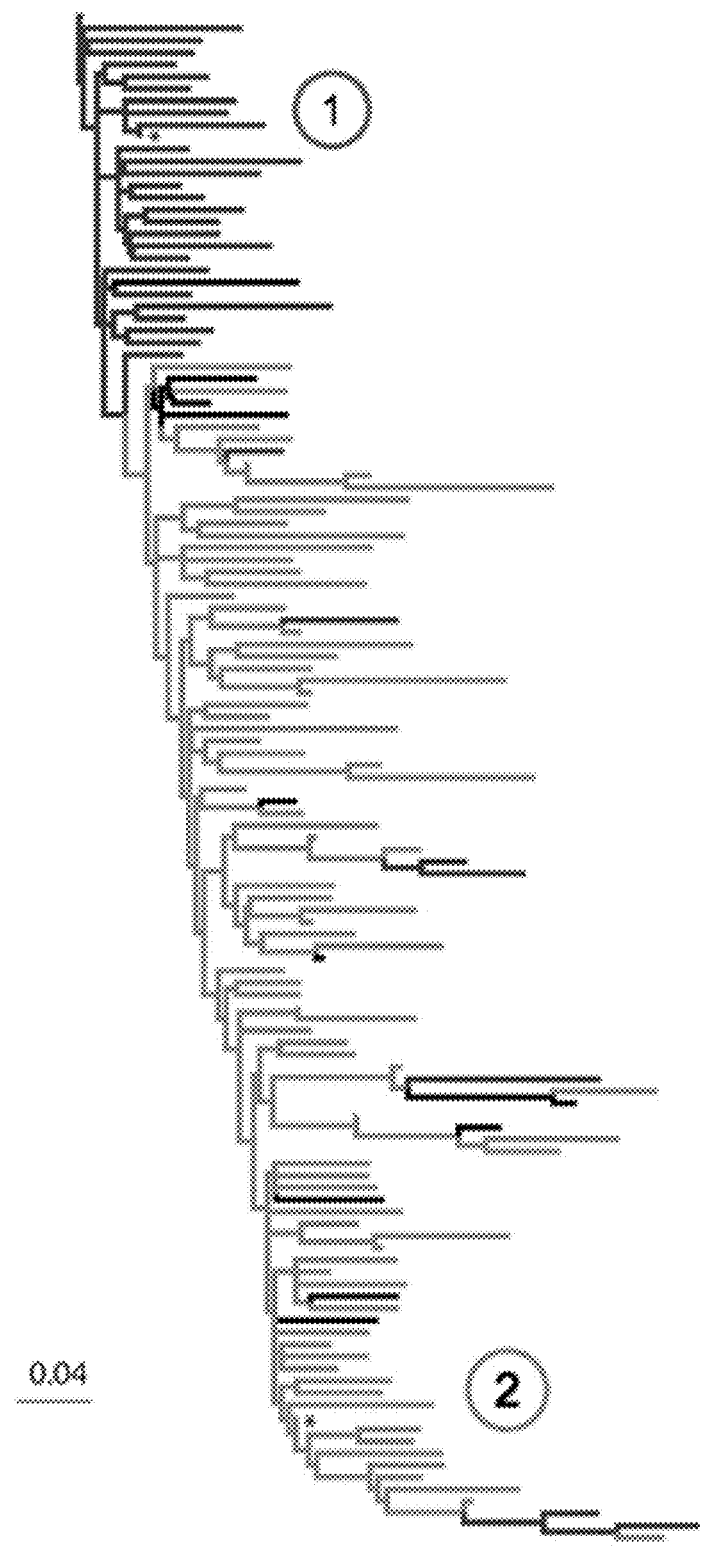
FIG. 3: Phylogenic analysis of BC2-4G. (A) Maximum likelihood phylogram of BC2-4G. Sub-lineages are defined by different CDR-H3 amino acid sequences. Black nodes represent CDR-H3 sequences that do not match one of the primary sub-lineage clusters. (B) Table illustrating the pairing specificity of CDR-H3 to CDR-L3 among dominant lineage members. (CARHGLGWDLYYFDYW, SEQ ID NO: 24; CQSYDSSLIGYVF; SEQ ID NO: 32; CQSYDASLKGYVF, SEQ ID NO: 33) (C-D) Representative VH and VL sequences for each pair denoted by '*' in (A). CDR1, CDR2, and CDR3 regions are underlined. (In C, VH4-59=SEQ ID NO: 81; in D, VL1-40=SEQ ID NO: 82)

Phylogenetic analysis of resident B cells in the SNs. Each SN sequencing database was mapped to a frequency-based mosaic plot as a first-pass filter to identify the clonally expanded and class-switched antibodies (FIG. 1B). Those expanded clonal lineages in the class-switched compartments were examined. From BC1, 1A, 2A, 3G and 4G were selected. From BC2, 1A, 2A, 3G, 4G and 5G were selected. Full-length heavy-chain sequences (VH genes) were constructed into maximum likelihood phylogenetic trees partitioned on the variable region IGHV gene segment. Clonal sub-lineages were then defined by clusters of VH genes containing identical CDR-H3 amino acid sequences (FIG. 2A). The BC2-3G phylogram diverged into 4 sub-lineages, each defined by a related, but unique, CDR-H3 amino acid sequence originating from the joining of the VH6-1, DH6-13, and JH4 gene segments (FIG. 2A). Furthermore, the paired sequencing data in FIG. 2B indicates that each CDR-H3 sub-lineage may prefer a specific CDR-L3 variant originating from a VK3-11 and JK4 light chain phylogeny. The observation that specific mutations appear linked across both VH and $V_L$ genes is highly suggestive of clonal expansion and somatic hypermutation consistent with antigen-driven affinity maturation in germinal centers (FIG. 2C, 2D). BC2-4G and BC2-5G clonal lineages also displayed this behavior, each with 2 major sub-lineages that utilized a single VH and VL gene combination (FIGS. 3-4).

Ig-Seq sample preparation. Full length NY-ESO-1 construct was expressed in a HIS-fusion bacterial expression system using the pET-28a expression vector (Novagen). Cultures were induced by the addition of isopropyl-p-D-thiogalactopyranoside (IPTG). 1 liter of IPTG-induced bacterial cell cultures were lysed using 5 cycles of sonication, followed by fusion protein solublization with 1% Tween-20 in PBS. The protein was purified under native conditions using HIS-Select® HF nickel affinity gel (Sigma) in batch processing format according to manufacturer's instructions. The purity was >90%, as determined by SDS-PAGE gel treated with EZBlue Gel staining reagent (Sigma). Protein concentration was determined by Bradford-based protein assay (BioRad) with an average yield of 0.5 mg per liter.

Total IgG (7.5 mg) was isolated from 1 mL plasma using Protein G Plus agarose (Thermo Fisher Scientific) affinity chromatography and cleaved into F(ab')2 fragments using IgeS (FabRICATOR; Genovis). NY-ESO-1 specific F(ab')2 was isolated by affinity chromatography using recombinant NY-ESO-1 coupled to NHS-activated agarose resin (Thermo Fisher Scientific). F(ab')2 was applied to the column in gravity mode with the flow-through collected. Following elution with 100 mM glycine-HCl pH 2.7 and neutralization, the protein-containing fractions were pooled.

LC-MS/MS sample preparation. Briefly, the antigen-specific elution and the non-specific flow-through were separately concentrated, denatured in 50% (v/v) TFE and 10 mM PBS, reduced with 2.5 mM DTT, and incubated at 55° C. for 45 min. The samples were then alkylated with 15 mM iodoacetamide (Sigma) for 30 min at RT in the dark. Each sample was diluted 10× with 40 mM Tris-HCl pH 8.0 and digested with trypsin (1:50 trypsin/protein) for 4 hrs at 37° C. Formic acid (1% v/v) was used to quench the digestion. The peptides were then concentrated under vacuum, resuspended in 5% acetonitrile and 0.1% formic acid, and washed on C18-SpinTips (Thermo Fisher Scientific) according to the manufacturer's instructions.

LC-MS/MS of NY-ESO-1 F(ab')2. The peptides were analyzed by liquid chromatography tandem mass spectrometry (LC-MS/MS) using a Dionex UltiMate 3000 RSLCnano reverse phase chromatography system (Dionex Acclaim PepMapRSLC C18 column; Thermo Scientific) coupled to an Orbitrap Velos Pro mass spectrometer (Thermo Scientific). Parent ion MS1 scans were collected in the Orbitrap at 60,000 resolution. Ions with >+1 charge were fragmented by collision-induced dissociation (NCE 35), with a maximum of 20 MS2 spectra collected per MS1. Ions selected twice in a 30-second window were dynamically excluded for 45 seconds. Both the elution and the flow through were run three times.

MS/MS data analysis. A patient-specific antibody database was constructed by appending the full length IgG VH sequences to a database of background proteins comprising patient-specific VL sequences, Ensembl human protein-coding sequences, and common contaminants (maxquant.org). The spectra were then searched against this database using SEQUEST (Proteome Discoverer 1.4, Thermo Scientific) as described (Lee et al., 2016). High confidence peptide spectrum matches (PSMs) were filtered with Percolator (Proteome Discoverer1.4) at a false discovery rate of <1%, and only peptides with an average mass deviation <1.5 ppm were retained for downstream analysis. The full-length VH IgG sequences were organized into protein groups using a single-linkage hierarchical clustering algorithm requiring ≥90% amino acid identity in the CDR-H3 as measured by edit distance (Lee et al., 2016); peptides mapping to only a single protein group were considered informative. The relative abundances of the corresponding protein groups were calculated as a sum of the extracted-ion chromatogram (XIC) peak area for informative CDR-H3-J region peptides.

LC-MS/MS spectra of NY-ESO-1-specific F(ab')2. The MS/MS spectra was evaluated using a custom machine learning system trained to recognize CDR-H3-J region peptide spectra. Built on a random forest classifier, this was trained in-house against a library of ~100,000 positive (CDR-H3-J) and negative (not CDR-H3-J) spectra collected in previous repertoire studies. Given an unknown spectrum, the custom machine learning system predicts whether that spectrum derived from a CDR-H3-J peptide. It performs independently of any sequence database and does not predict the peptide sequence.

Figures 2E, 2F:
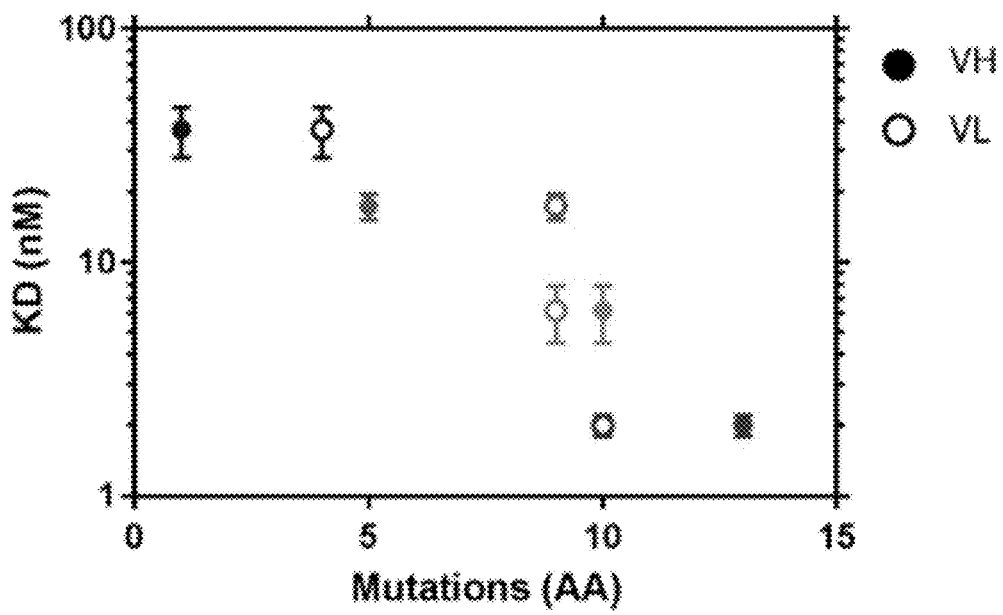

The spectra were identified using the donor specific B-cell receptor sequence database generated from the SN. The abundance of each lineage was measured by the intensity of the CDR-H3-J region peptide. The presence of BC2-3G and BC2-4G lineages was confirmed in the plasma. The relative abundances of the plasma response to NY-ESO-1 indicated the presence of all 4 distinct sub-lineages of the BC2-3G lineage (shown in FIG. 2A) and both sub-lineages of BC2-4G. FIG. 2F illustrates the observed peptide coverage for BC2-3G lineage 1. CDR-H3 peptide is unique to the BC2-3G lineage, while many other peptides were observed across multiple lineages due to their low mutation rate.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 9,708,654
U.S. Pat. No. 9,090,674
International PCT Patent application No. WO2017127510
Bolger et al., *Bioinformatics*, 30(15):2114-20, 2014.
Bolotin et al., *Nat Methods*, 12(5):380-1, 2015.
Katoh et al., *Nucleic Acids Res.*, 30(14):3059-66, 2002.
Lee et al., *Nat Med.*, 22(12):1456-64, 2016.
Lee et al., *Nat Immunol.*, 18(8):889-898, 2017.
McDaniel et al., *Cancer Immunol Immunother*, 67(5):729-738, 2018.
Plotly Technologies Inc., https: plot.ly2015.
Stamatakis, *Bioinformatics*. 30(9):1312-3, 2014.
Zhang et al., *Bioinformatics*, 30(5):614-20, 2014.

What is claimed is:

1. An isolated monoclonal antibody, wherein the antibody specifically binds to NY-ESO-1 and comprises:
   (i) a heavy chain variable region (VH) comprising a VHCDR1 amino acid sequence of SEQ ID NO: 1, a VHCDR2 amino acid sequence of SEQ ID NO: 3, and a VHCDR3 amino acid sequence of SEQ ID NO: 16; and a light chain variable region (VL) comprising a VLCDR1 amino acid sequence of SEQ ID NO: 10, a VLCDR2 amino acid sequence of SEQ ID NO: 12, and a VLCDR3 amino acid sequence of SEQ ID NO: 17;
   (ii) a heavy chain variable region (VH) comprising a VHCDR1 amino acid sequence of SEQ ID NO: 1, a VHCDR2 amino acid sequence of SEQ ID NO: 3, and a VHCDR3 amino acid sequence of SEQ ID NO: 6; and a light chain variable region (VL) comprising a VLCDR1 amino acid sequence of SEQ ID NO: 10, a VLCDR2 amino acid sequence of SEQ ID NO: 12, and a VLCDR3 amino acid sequence of SEQ ID NO: 13;
   (iii) a heavy chain variable region (VH) comprising a VHCDR1 amino acid sequence of SEQ ID NO: 1, a VHCDR2 amino acid sequence of SEQ ID NO: 4, and a VHCDR3 amino acid sequence of SEQ ID NO: 7; and a light chain variable region (VL) comprising a VLCDR1 amino acid sequence of SEQ ID NO: 11, a VLCDR2 amino acid sequence of SEQ ID NO: 12, and a VLCDR3 amino acid sequence of SEQ ID NO: 14;
   (iv) a heavy chain variable region (VH) comprising a VHCDR1 amino acid sequence of SEQ ID NO: 1, a VHCDR2 amino acid sequence of SEQ ID NO: 4, and a VHCDR3 amino acid sequence of SEQ ID NO: 8; and a light chain variable region (VL) comprising a VLCDR1 amino acid sequence of SEQ ID NO: 11, a VLCDR2 amino acid sequence of SEQ ID NO: 12, and a VLCDR3 amino acid sequence of SEQ ID NO: 14;
   (v) a heavy chain variable region (VH) comprising a VHCDR1 amino acid sequence of SEQ ID NO: 2, a VHCDR2 amino acid sequence of SEQ ID NO: 5, and a VHCDR3 amino acid sequence of SEQ ID NO: 9; and a light chain variable region (VL) comprising a VLCDR1 amino acid sequence of SEQ ID NO: 11, a VLCDR2 amino acid sequence of SEQ ID NO: 12, and a VLCDR3 amino acid sequence of SEQ ID NO: 15;
   (vi) a heavy chain variable region (VH) comprising a VHCDR1 amino acid sequence of SEQ ID NO: 18, a VHCDR2 amino acid sequence of SEQ ID NO: 21, and a VHCDR3 amino acid sequence of SEQ ID NO: 24; and a light chain variable region (VL) comprising a VLCDR1 amino acid sequence of SEQ ID NO: 26, a VLCDR2 amino acid sequence of SEQ ID NO: 28, and a VLCDR3 amino acid sequence of SEQ ID NO: 31;
   (vii) a heavy chain variable region (VH) comprising a VHCDR1 amino acid sequence of SEQ ID NO: 19, a VHCDR2 amino acid sequence of SEQ ID NO: 22, and a VHCDR3 amino acid sequence of SEQ ID NO: 24; and a light chain variable region (VL) comprising a VLCDR1 amino acid sequence of SEQ ID NO: 26, a VLCDR2 amino acid sequence of SEQ ID NO: 29, and a VLCDR3 amino acid sequence of SEQ ID NO: 32;
   (viii) a heavy chain variable region (VH) comprising a VHCDR1 amino acid sequence of SEQ ID NO: 20, a VHCDR2 amino acid sequence of SEQ ID NO: 23, and a VHCDR3 amino acid sequence of SEQ ID NO: 25; and a light chain variable region (VL) comprising a VLCDR1 amino acid sequence of SEQ ID NO: 27, a VLCDR2 amino acid sequence of SEQ ID NO: 30, and a VLCDR3 amino acid sequence of SEQ ID NO: 33;
   (ix) a heavy chain variable region (VH) comprising a VHCDR1 amino acid sequence of SEQ ID NO: 34, a VHCDR2 amino acid sequence of SEQ ID NO: 35, and a VHCDR3 amino acid sequence of SEQ ID NO: 44; and a light chain variable region (VL) comprising a VLCDR1 amino acid sequence of SEQ ID NO: 38, a VLCDR2 amino acid sequence of SEQ ID NO: 40, and a VLCDR3 amino acid sequence of SEQ ID NO: 42; or
   (x) a heavy chain variable region (VH) comprising a VHCDR1 amino acid sequence of SEQ ID NO: 34, a VHCDR2 amino acid sequence of SEQ ID NO: 36, and a VHCDR3 amino acid sequence of SEQ ID NO: 37; and a light chain variable region (VL) comprising a VLCDR1 amino acid sequence of SEQ ID NO: 39, a VLCDR2 amino acid sequence of SEQ ID NO: 41, and a VLCDR3 amino acid sequence of SEQ ID NO: 43.

2. The antibody of claim 1, wherein the antibody is an IgG antibody, an IgM antibody, an IgA antibody, an IgE antibody, or an antigen binding fragment thereof.

3. The antibody of claim 1, wherein the antibody is a Fab', a F(ab')2, a F(ab')3, a monovalent scFv, or a bivalent scFv.

4. The antibody of claim 1, wherein the antibody is a human antibody, a humanized antibody, or a de-immunized antibody.

5. A chimeric antigen receptor (CAR) protein, wherein the CAR protein binds NY-ESO-1 and comprises:
   (i) a heavy chain variable region (VH) comprising a VHCDR1 amino acid sequence of SEQ ID NO: 1, a VHCDR2 amino acid sequence of SEQ ID NO: 3, and a VHCDR3 amino acid sequence of SEQ ID NO: 16; and a light chain variable region (VL) comprising a VLCDR1 amino acid sequence of SEQ ID NO: 10, a VLCDR2 amino acid sequence of SEQ ID NO: 12, and a VLCDR3 amino acid sequence of SEQ ID NO: 17;
   (ii) a heavy chain variable region (VH) comprising a VHCDR1 amino acid sequence of SEQ ID NO: 1, a VHCDR2 amino acid sequence of SEQ ID NO: 3, and a VHCDR3 amino acid sequence of SEQ ID NO: 6; and a light chain variable region (VL) comprising a VLCDR1 amino acid sequence of SEQ ID NO: 10, a VLCDR2 amino acid sequence of SEQ ID NO: 12, and a VLCDR3 amino acid sequence of SEQ ID NO: 13;
   (iii) a heavy chain variable region (VH) comprising a VHCDR1 amino acid sequence of SEQ ID NO: 1, a VHCDR2 amino acid sequence of SEQ ID NO: 4, and a VHCDR3 amino acid sequence of SEQ ID NO: 7; and a light chain variable region (VL) comprising a VLCDR1 amino acid sequence of SEQ ID NO: 11, a VLCDR2 amino acid sequence of SEQ ID NO: 12, and a VLCDR3 amino acid sequence of SEQ ID NO: 14;
   (iv) a heavy chain variable region (VH) comprising a VHCDR1 amino acid sequence of SEQ ID NO: 1, a VHCDR2 amino acid sequence of SEQ ID NO: 4, and a VHCDR3 amino acid sequence of SEQ ID NO: 8; and a light chain variable region (VL) comprising a VLCDR1 amino acid sequence of SEQ ID NO: 11, a VLCDR2 amino acid sequence of SEQ ID NO: 12, and a VLCDR3 amino acid sequence of SEQ ID NO: 14;
   (v) a heavy chain variable region (VH) comprising a VHCDR1 amino acid sequence of SEQ ID NO: 2, a VHCDR2 amino acid sequence of SEQ ID NO: 5, and a VHCDR3 amino acid sequence of SEQ ID NO: 9; and a light chain variable region (VL) comprising a VLCDR1 amino acid sequence of SEQ ID NO: 11, a VLCDR2 amino acid sequence of SEQ ID NO: 12, and a VLCDR3 amino acid sequence of SEQ ID NO: 15;

(vi) a heavy chain variable region (VH) comprising a VHCDR1 amino acid sequence of SEQ ID NO: 18, a VHCDR2 amino acid sequence of SEQ ID NO: 21, and a VHCDR3 amino acid sequence of SEQ ID NO: 24; and a light chain variable region (VL) comprising a VLCDR1 amino acid sequence of SEQ ID NO: 26, a VLCDR2 amino acid sequence of SEQ ID NO: 28, and a VLCDR3 amino acid sequence of SEQ ID NO: 31;

(vii) a heavy chain variable region (VH) comprising a VHCDR1 amino acid sequence of SEQ ID NO: 19, a VHCDR2 amino acid sequence of SEQ ID NO: 22, and a VHCDR3 amino acid sequence of SEQ ID NO: 24; and a light chain variable region (VL) comprising a VLCDR1 amino acid sequence of SEQ ID NO: 26, a VLCDR2 amino acid sequence of SEQ ID NO: 29, and a VLCDR3 amino acid sequence of SEQ ID NO: 32;

(viii) a heavy chain variable region (VH) comprising a VHCDR1 amino acid sequence of SEQ ID NO: 20, a VHCDR2 amino acid sequence of SEQ ID NO: 23, and a VHCDR3 amino acid sequence of SEQ ID NO: 25; and a light chain variable region (VL) comprising a VLCDR1 amino acid sequence of SEQ ID NO: 27, a VLCDR2 amino acid sequence of SEQ ID NO: 30, and a VLCDR3 amino acid sequence of SEQ ID NO: 33;

(ix) a heavy chain variable region (VH) comprising a VHCDR1 amino acid sequence of SEQ ID NO: 34, a VHCDR2 amino acid sequence of SEQ ID NO: 35, and a VHCDR3 amino acid sequence of SEQ ID NO: 44; and a light chain variable region (VL) comprising a VLCDR1 amino acid sequence of SEQ ID NO: 38, a VLCDR2 amino acid sequence of SEQ ID NO: 40, and a VLCDR3 amino acid sequence of SEQ ID NO: 42; or (x) a heavy chain variable region (VH) comprising a VHCDR1 amino acid sequence of SEQ ID NO: 34, a VHCDR2 amino acid sequence of SEQ ID NO: 36, and a VHCDR3 amino acid sequence of SEQ ID NO: 37; and a light chain variable region (VL) comprising a VLCDR1 amino acid sequence of SEQ ID NO: 39, a VLCDR2 amino acid sequence of SEQ ID NO: 41, and a VLCDR3 amino acid sequence of SEQ ID NO: 43.

6. A polynucleotide molecule encoding a CAR protein according to claim 5.

7. An engineered cell comprising a polynucleotide molecule according to claim 6.

8. The engineered cell of claim 7, wherein the engineered cell is a T cell.

9. The engineered cell of claim 8, wherein the T cell is a cytotoxic T cell.

10. The antibody of claim 1, wherein the antibody is conjugated to an imaging agent, a chemotherapeutic agent, a toxin, or a radionuclide.

11. A composition comprising an antibody of claim 1 in a pharmaceutically acceptable carrier.

* * * * *

UNITED STATES PATENT AND TRADEMARK OFFICE
CERTIFICATE OF CORRECTION

PATENT NO. : 11,866,785 B2
APPLICATION NO. : 16/759371
DATED : January 9, 2024
INVENTOR(S) : Gregory C. Ippolito et al.

It is certified that error appears in the above-identified patent and that said Letters Patent is hereby corrected as shown below:

On the Title Page

(56) References Cited – Foreign Patent Documents, delete "WO WO 2016/176322 11/2006" and insert --WO WO 2016/176322 11/2016-- therefor.

(56) References Cited – Foreign Patent Documents, delete "WO WO 2016/210365 12/1916" and insert --WO WO 2016/210365 12/2016-- therefor.

(56) References Cited – Foreign Patent Documents, delete "WO WO 2017/044661 3/1917" and insert --WO WO 2017/044661 3/2017-- therefor.

(56) References Cited – Foreign Patent Documents, delete "WO WO 2017/127510 7/1917" and insert --WO WO 2017/127510 7/2017-- therefor.

(56) References Cited – Foreign Patent Documents, delete "WO WO 2017/173321 10/1917" and insert --WO WO 2017/173321 10/2017-- therefor.

Signed and Sealed this
Fourteenth Day of May, 2024

Katherine Kelly Vidal
*Director of the United States Patent and Trademark Office*